(12) United States Patent
Pimenta et al.

(10) Patent No.: US 9,351,845 B1
(45) Date of Patent: *May 31, 2016

(54) METHOD AND APPARATUS FOR PERFORMING SPINE SURGERY

(75) Inventors: Luiz Pimenta, Sao Paulo (BR); Michael Serra, San Diego, CA (US); Andrew Morris, San Diego, CA (US); Nathan Lovell, Encinitas, CA (US); Nelson Oi, San Diego, CA (US); Eugene Shoshtaev, La Jolla, CA (US)

(73) Assignee: NuVasive, Inc., San Diego, CA (US)

( * ) Notice: Subject to any disclaimer, the term of this patent is extended or adjusted under 35 U.S.C. 154(b) by 1113 days.

This patent is subject to a terminal disclaimer.

(21) Appl. No.: 13/077,977

(22) Filed: Mar. 31, 2011

Related U.S. Application Data

(63) Continuation-in-part of application No. 12/799,021, filed on Apr. 16, 2010, now Pat. No. 8,287,597.

(60) Provisional application No. 61/212,921, filed on Apr. 16, 2009, provisional application No. 61/319,823, filed on Mar. 31, 2010, provisional application No. 61/357,951, filed on Jun. 23, 2010.

(51) Int. Cl.
*A61B 18/12* (2006.01)
*A61F 2/44* (2006.01)
(Continued)

(52) U.S. Cl.
CPC .............. *A61F 2/442* (2013.01); *A61B 17/0206* (2013.01); *A61B 17/3209* (2013.01); *A61B 17/3211* (2013.01); *A61B 17/320016* (2013.01);
(Continued)

(58) Field of Classification Search
CPC ........ A61B 18/18; A61B 18/14; A61B 18/22; A61B 18/148; A61B 18/08; A61B 2018/00565; A61B 2018/0044; A61B 2018/00339; A61B 17/3211; A61B 17/0206; A61B 17/0218; A61B 17/16; A61B 2017/0256; A61B 2017/32113; A61B 1/32; A61F 2/4611; A61F 2/442; A61F 2/4425
USPC ....... 606/201–219, 279, 33, 41, 45, 86 A, 99; 623/17.11–17.16; 600/201–246
See application file for complete search history.

(56) References Cited

U.S. PATENT DOCUMENTS

| 208,227 A | 9/1900 | Dorr |
| 972,983 A | 10/1910 | Arthur |

(Continued)

FOREIGN PATENT DOCUMENTS

| CA | 2015507 | 5/1999 |
| DE | 29908259 | 7/1999 |

(Continued)

OTHER PUBLICATIONS

"510(k) for Neurovision JJB System (Summary)", NuVasive Letter, (Sep. 25, 2001), 28 pgs.

(Continued)

*Primary Examiner* — Michael Peffley
*Assistant Examiner* — Daniel Fowler
(74) *Attorney, Agent, or Firm* — Jennifer Russell

(57) ABSTRACT

Systems and methods are described for correcting sagittal imbalance in a spine including instruments for performing the controlled release of the anterior longitudinal ligament through a lateral access corridor and hyper-lordotic lateral implants.

22 Claims, 23 Drawing Sheets

(51) Int. Cl.
*A61B 17/34* (2006.01)
*A61B 17/02* (2006.01)
*A61B 17/3209* (2006.01)
*A61B 17/3211* (2006.01)
*A61F 2/46* (2006.01)
*A61B 17/32* (2006.01)
*A61F 2/30* (2006.01)
*A61F 2/28* (2006.01)
*A61B 17/00* (2006.01)

(52) U.S. Cl.
CPC ............. *A61B 17/3421* (2013.01); *A61F 2/447* (2013.01); *A61F 2/4455* (2013.01); *A61F 2/4611* (2013.01); *A61B 17/320036* (2013.01); *A61B 2017/00261* (2013.01); *A61B 2017/0262* (2013.01); *A61F 2002/2817* (2013.01); *A61F 2002/3093* (2013.01); *A61F 2002/30281* (2013.01); *A61F 2002/30576* (2013.01); *A61F 2002/30784* (2013.01); *A61F 2002/30787* (2013.01); *A61F 2002/30904* (2013.01); *A61F 2310/00359* (2013.01)

(56) References Cited

U.S. PATENT DOCUMENTS

| | | |
|---|---|---|
| 1,328,624 A | 1/1920 | Graham |
| 1,548,184 A | 8/1925 | Cameron |
| 2,704,064 A | 3/1955 | Fizzell |
| 2,736,002 A | 2/1956 | Oriel |
| 2,808,826 A | 10/1957 | Reiner |
| 3,364,929 A | 1/1968 | Ide |
| 3,486,505 A | 12/1969 | Morrison |
| 3,518,993 A | 7/1970 | Blake |
| 3,604,487 A | 9/1971 | Gilbert |
| 3,664,329 A | 5/1972 | Naylor |
| 3,682,162 A | 8/1972 | Colyer |
| 3,745,995 A | 7/1973 | Kraus |
| 3,785,368 A | 1/1974 | McCarthy |
| 3,830,226 A | 8/1974 | Staub |
| 3,848,601 A | 11/1974 | Ma |
| 3,867,728 A | 2/1975 | Stubstad |
| 3,957,036 A | 5/1976 | Normann |
| 4,026,304 A | 5/1977 | Levy |
| 4,026,305 A | 5/1977 | Brownlee |
| 4,099,519 A | 7/1978 | Warren |
| 4,164,214 A | 8/1979 | Stark |
| 4,207,897 A | 6/1980 | Lloyd |
| 4,224,949 A | 9/1980 | Scott |
| 4,226,228 A | 10/1980 | Shin |
| 4,235,242 A | 11/1980 | Howson |
| 4,285,347 A | 8/1981 | Hess |
| 4,291,705 A | 9/1981 | Severinghaus |
| 4,461,300 A | 7/1984 | Christensen |
| 4,501,269 A | 2/1985 | Bagby |
| 4,515,168 A | 5/1985 | Chester |
| 4,519,403 A | 5/1985 | Dickhudt |
| 4,545,374 A | 10/1985 | Jacobson |
| 4,561,445 A | 12/1985 | Berke |
| 4,562,832 A | 1/1986 | Wilder |
| 4,573,448 A | 3/1986 | Kambin |
| 4,592,369 A | 6/1986 | Davis |
| 4,595,018 A | 6/1986 | Rantala |
| 4,611,597 A | 9/1986 | Kraus |
| 4,633,889 A | 1/1987 | Talalla |
| 4,646,738 A | 3/1987 | Trott |
| 4,657,550 A | 4/1987 | Daher |
| 4,658,835 A | 4/1987 | Pohndorf |
| 4,743,256 A | 5/1988 | Brantigan |
| 4,744,371 A | 5/1988 | Harris |
| 4,759,377 A | 7/1988 | Dykstra |
| 4,759,769 A * | 7/1988 | Hedman et al. ............ 623/17.13 |
| 4,781,591 A | 11/1988 | Allen |
| 4,784,150 A | 11/1988 | Voorhies |
| 4,807,642 A | 2/1989 | Brown |
| 4,834,757 A | 5/1989 | Brantigan |
| 4,877,020 A | 10/1989 | Vich |
| 4,878,915 A | 11/1989 | Brantigan |
| 4,892,105 A | 1/1990 | Prass |
| 4,913,134 A | 4/1990 | Luque |
| 4,926,865 A | 5/1990 | Oman |
| 4,932,975 A | 6/1990 | Main |
| 4,950,296 A | 8/1990 | McIntyre |
| 4,961,740 A | 10/1990 | Ray |
| 4,962,766 A | 10/1990 | Herzon |
| 4,964,411 A | 10/1990 | Johnson |
| 5,007,902 A | 4/1991 | Witt |
| 5,015,247 A | 5/1991 | Michelson |
| 5,026,373 A | 6/1991 | Ray |
| 5,047,055 A | 9/1991 | Bao |
| 5,052,373 A | 10/1991 | Michelson |
| 5,055,104 A | 10/1991 | Ray |
| 5,058,602 A | 10/1991 | Brody |
| 5,062,845 A | 11/1991 | Kuslich |
| 5,071,437 A | 12/1991 | Steffee |
| 5,081,990 A | 1/1992 | Deletis |
| 5,092,344 A | 3/1992 | Lee |
| 5,092,572 A | 3/1992 | Litwak |
| 5,127,403 A | 7/1992 | Brownlee |
| 5,133,717 A | 7/1992 | Chopin |
| 5,133,755 A | 7/1992 | Brekke |
| 5,161,533 A | 11/1992 | Prass |
| 5,171,278 A | 12/1992 | Pisharodi |
| 5,171,279 A | 12/1992 | Mathews |
| 5,192,327 A | 3/1993 | Brantigan |
| 5,195,541 A | 3/1993 | Obenchain |
| 5,196,015 A | 3/1993 | Neubardt |
| 5,217,497 A | 6/1993 | Mehdian |
| RE34,390 E | 9/1993 | Culver |
| 5,255,691 A | 10/1993 | Otten |
| 5,263,953 A | 11/1993 | Bagby |
| 5,269,785 A | 12/1993 | Bonutti |
| 5,282,468 A | 2/1994 | Klepinski |
| 5,284,153 A | 2/1994 | Raymond |
| 5,284,154 A | 2/1994 | Raymond |
| 5,290,494 A | 3/1994 | Coombes |
| 5,295,994 A | 3/1994 | Bonutti |
| 5,299,563 A | 4/1994 | Seton |
| 5,300,076 A | 4/1994 | Leriche |
| 5,304,210 A | 4/1994 | Crook |
| 5,306,307 A | 4/1994 | Senter |
| 5,306,309 A | 4/1994 | Wagner |
| 5,312,417 A | 5/1994 | Wilk |
| 5,313,956 A | 5/1994 | Knutsson |
| 5,313,962 A | 5/1994 | Obenchain |
| 5,322,505 A | 6/1994 | Krause |
| 5,327,902 A | 7/1994 | Lemmen |
| 5,331,975 A | 7/1994 | Bonutti |
| 5,333,618 A | 8/1994 | Lekhtman |
| 5,334,205 A | 8/1994 | Cain |
| 5,336,223 A | 8/1994 | Rogers |
| 5,342,384 A | 8/1994 | Sugarbaker |
| 5,364,400 A | 11/1994 | Rego, Jr. |
| 5,375,067 A | 12/1994 | Berchin |
| 5,375,594 A | 12/1994 | Cueva |
| 5,383,876 A | 1/1995 | Nardella |
| 5,395,317 A | 3/1995 | Kambin |
| 5,395,372 A | 3/1995 | Holt |
| 5,397,363 A | 3/1995 | Gelbard |
| 5,397,364 A | 3/1995 | Kozak |
| 5,405,391 A | 4/1995 | Hednerson |
| 5,413,602 A | 5/1995 | Metz-Stavenhagen |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen |
| 5,445,639 A | 8/1995 | Kuslich |
| 5,450,845 A | 9/1995 | Axelgaard |
| 5,454,811 A | 10/1995 | Huebner |
| 5,458,638 A | 10/1995 | Kuslich |
| 5,458,642 A * | 10/1995 | Beer et al. .................. 623/17.13 |
| 5,474,057 A | 12/1995 | Makower |
| 5,474,558 A | 12/1995 | Neubardt |

(56) References Cited

U.S. PATENT DOCUMENTS

| | | |
|---|---|---|
| 5,480,440 A | 1/1996 | Kambin |
| 5,482,038 A | 1/1996 | Ruff |
| 5,484,403 A | 1/1996 | Yoakum |
| 5,484,437 A | 1/1996 | Michelson |
| 5,489,307 A | 2/1996 | Kuslich |
| 5,489,308 A | 2/1996 | Kuslich |
| 5,509,893 A | 4/1996 | Pracas |
| 5,514,153 A | 5/1996 | Bonutti |
| 5,514,180 A | 5/1996 | Heggeness |
| 5,522,879 A | 6/1996 | Scopelianos |
| 5,522,899 A | 6/1996 | Michelson |
| 5,524,624 A | 6/1996 | Tepper |
| 5,527,312 A | 6/1996 | Ray |
| 5,534,030 A | 7/1996 | Navarro |
| 5,540,235 A | 7/1996 | Wilson |
| 5,540,688 A | 7/1996 | Navas |
| 5,545,222 A | 8/1996 | Bonutti |
| 5,549,656 A | 8/1996 | Reiss |
| 5,560,372 A | 10/1996 | Cory |
| 5,562,736 A | 10/1996 | Ray |
| 5,565,005 A | 10/1996 | Erickson |
| 5,566,678 A | 10/1996 | Cadwell |
| 5,571,149 A | 11/1996 | Liss |
| 5,571,190 A | 11/1996 | Ulrich |
| 5,571,192 A | 11/1996 | Schonhoffer |
| 5,579,781 A | 12/1996 | Cooke |
| 5,593,409 A | 1/1997 | Michelson |
| 5,593,429 A | 1/1997 | Ruff |
| 5,599,279 A | 2/1997 | Slotman |
| 5,609,636 A | 3/1997 | Kohrs |
| 5,611,800 A | 3/1997 | Davis |
| 5,611,810 A | 3/1997 | Arnold |
| 5,630,813 A | 5/1997 | Kieturakis |
| 5,632,747 A | 5/1997 | Scarborough |
| 5,645,598 A | 7/1997 | Brosnahan |
| 5,653,761 A | 8/1997 | Pisharodi |
| 5,653,762 A | 8/1997 | Pisharodi |
| 5,658,336 A | 8/1997 | Pisharodi |
| 5,658,337 A | 8/1997 | Kohrs |
| 5,662,710 A | 9/1997 | Bonutti |
| 5,665,122 A | 9/1997 | Kambin |
| 5,667,508 A | 9/1997 | Errico |
| 5,669,909 A | 9/1997 | Zdeblick |
| 5,671,752 A | 9/1997 | Sinderby |
| 5,676,703 A | 10/1997 | Gelbard |
| 5,681,265 A | 10/1997 | Maeda |
| 5,683,394 A | 11/1997 | Rinner |
| 5,683,400 A | 11/1997 | McGuire |
| 5,683,464 A | 11/1997 | Wagner |
| 5,690,629 A | 11/1997 | Asher |
| 5,700,264 A | 12/1997 | Zucherman |
| 5,700,291 A | 12/1997 | Kuslich |
| 5,700,292 A | 12/1997 | Margulies |
| 5,702,449 A | 12/1997 | McKay |
| 5,702,451 A | 12/1997 | Biedermann |
| 5,702,453 A | 12/1997 | Rabbe |
| 5,702,454 A | 12/1997 | Baumgartner |
| 5,702,455 A | 12/1997 | Saggar |
| 5,703,451 A | 12/1997 | Yamamichi |
| 5,707,359 A | 1/1998 | Bufalini |
| 5,707,373 A | 1/1998 | Sevrain |
| 5,711,307 A | 1/1998 | Smits |
| 5,711,957 A | 1/1998 | Patat |
| 5,716,415 A | 2/1998 | Steffee |
| 5,720,748 A | 2/1998 | Kuslich |
| 5,720,751 A | 2/1998 | Jackson |
| 5,728,046 A | 3/1998 | Mayer |
| 5,728,159 A | 3/1998 | Stroever |
| 5,741,253 A | 4/1998 | Michelson |
| 5,741,261 A | 4/1998 | Moskovitz |
| 5,755,797 A | 5/1998 | Baumgartner |
| 5,759,159 A | 6/1998 | Masreliez |
| 5,762,629 A | 6/1998 | Kambin |
| 5,766,252 A | 6/1998 | Henry |
| 5,772,661 A | 6/1998 | Michelson |
| 5,775,331 A | 7/1998 | Raymond |
| 5,775,797 A | 7/1998 | Henstra |
| 5,776,144 A | 7/1998 | Leysieffer |
| 5,779,642 A | 7/1998 | Nightengale |
| 5,782,830 A | 7/1998 | Farris |
| 5,782,919 A | 7/1998 | Zdeblick |
| 5,785,658 A | 7/1998 | Benaron |
| 5,785,707 A * | 7/1998 | Boyd et al. ............... 606/41 |
| 5,785,710 A | 7/1998 | Michelson |
| 5,792,044 A | 8/1998 | Foley |
| 5,797,854 A | 8/1998 | Hedgecock |
| 5,797,909 A | 8/1998 | Michelson |
| 5,800,549 A | 9/1998 | Bao |
| 5,800,550 A | 9/1998 | Sertich |
| 5,814,073 A | 9/1998 | Bonutti |
| 5,814,084 A | 9/1998 | Grivas |
| 5,830,151 A | 11/1998 | Hadzic |
| 5,851,191 A | 12/1998 | Gozani |
| 5,851,208 A | 12/1998 | Trott |
| 5,853,373 A | 12/1998 | Griffith |
| 5,860,973 A | 1/1999 | Michelson |
| 5,862,314 A | 1/1999 | Jeddeloh |
| 5,865,845 A | 2/1999 | Thalgott |
| 5,865,848 A | 2/1999 | Baker |
| 5,872,314 A | 2/1999 | Clinton |
| 5,885,210 A | 3/1999 | Cox |
| 5,885,219 A | 3/1999 | Nightengale |
| 5,885,299 A | 3/1999 | Winslow |
| 5,888,196 A | 3/1999 | Bonutti |
| 5,888,219 A | 3/1999 | Bonutti |
| 5,888,224 A | 3/1999 | Beckers |
| 5,891,147 A | 4/1999 | Moskovitz |
| 5,893,890 A | 4/1999 | Pisharodi |
| 5,902,231 A | 5/1999 | Foley |
| 5,904,719 A | 5/1999 | Errico |
| 5,910,315 A | 6/1999 | Stevenson |
| 5,928,139 A | 7/1999 | Koros |
| 5,928,158 A | 7/1999 | Aristides |
| 5,931,777 A | 8/1999 | Sava |
| 5,935,131 A | 8/1999 | Bonutti |
| 5,938,688 A | 8/1999 | Schiff |
| 5,942,698 A | 8/1999 | Stevens |
| 5,944,658 A | 8/1999 | Koros |
| 5,954,769 A | 9/1999 | Rosenlicht |
| 5,968,098 A | 10/1999 | Winslow |
| 5,976,094 A | 11/1999 | Gozani |
| 5,993,474 A | 11/1999 | Ouchi |
| 6,003,426 A | 12/1999 | Kobayashi |
| 6,004,262 A | 12/1999 | Putz |
| 6,004,312 A | 12/1999 | Finneran |
| 6,004,326 A | 12/1999 | Castro |
| 6,007,487 A | 12/1999 | Foley |
| 6,008,433 A | 12/1999 | Stone |
| 6,015,436 A | 1/2000 | Schonhoffer |
| 6,024,696 A | 2/2000 | Hoftman |
| 6,027,456 A | 2/2000 | Feler |
| 6,033,405 A | 3/2000 | Winslow |
| 6,038,469 A | 3/2000 | Karlsson |
| 6,038,477 A | 3/2000 | Kayyali |
| 6,039,761 A | 3/2000 | Li |
| 6,042,582 A | 3/2000 | Ray |
| 6,045,580 A | 4/2000 | Scarborough |
| 6,048,342 A | 4/2000 | Zucherman |
| 6,050,992 A | 4/2000 | Nichols |
| 6,059,829 A | 5/2000 | Schläpfer |
| 6,063,088 A | 5/2000 | Winslow |
| 6,074,343 A | 6/2000 | Nathanson |
| 6,083,154 A | 7/2000 | Liu |
| 6,083,225 A | 7/2000 | Winslow |
| 6,095,987 A | 8/2000 | Shmulewitz |
| 6,096,080 A | 8/2000 | Nicholson |
| 6,102,948 A | 8/2000 | Brosnahan |
| 6,104,957 A | 8/2000 | Alo |
| 6,104,960 A | 8/2000 | Duysens |
| 6,120,503 A | 9/2000 | Michelson |
| 6,120,506 A | 9/2000 | Kohrs |
| 6,126,660 A | 10/2000 | Dietz |
| 6,132,386 A | 10/2000 | Gozani |
| 6,132,387 A | 10/2000 | Gozani |

(56) References Cited

U.S. PATENT DOCUMENTS

| | | | |
|---|---|---|---|
| 6,132,472 A | 10/2000 | Bonutti | |
| 6,135,965 A | 10/2000 | Turner | |
| 6,139,493 A | 10/2000 | Koros | |
| 6,143,033 A | 11/2000 | Paul | |
| 6,146,335 A | 11/2000 | Gozani | |
| 6,146,421 A * | 11/2000 | Gordon et al. | 623/17.15 |
| 6,146,422 A * | 11/2000 | Lawson | 623/17.16 |
| 6,152,871 A | 11/2000 | Foley | |
| 6,159,211 A | 12/2000 | Boriani | |
| 6,159,215 A | 12/2000 | Camino | |
| 6,161,047 A | 12/2000 | King | |
| 6,174,311 B1 | 1/2001 | Branch | |
| 6,181,961 B1 | 1/2001 | Prass | |
| 6,193,756 B1 | 2/2001 | Studer | |
| 6,196,969 B1 | 3/2001 | Bester | |
| 6,200,347 B1 | 3/2001 | Anderson | |
| 6,206,826 B1 | 3/2001 | Mathews | |
| 6,217,509 B1 | 4/2001 | Foley | |
| 6,224,549 B1 | 5/2001 | Drongelen | |
| 6,224,607 B1 | 5/2001 | Michelson | |
| 6,224,631 B1 | 5/2001 | Kohrs | |
| 6,231,571 B1 * | 5/2001 | Ellman et al. | 606/41 |
| 6,235,059 B1 | 5/2001 | Benezech | |
| 6,241,769 B1 | 6/2001 | Nicholson | |
| 6,241,771 B1 | 6/2001 | Gresser | |
| 6,251,140 B1 | 6/2001 | Marino | |
| 6,258,125 B1 | 7/2001 | Paul | |
| 6,259,945 B1 | 7/2001 | Epstein | |
| 6,264,651 B1 | 7/2001 | Underwood | |
| 6,266,558 B1 | 7/2001 | Gozani | |
| 6,273,905 B1 | 8/2001 | Streeter | |
| 6,277,149 B1 | 8/2001 | Boyle | |
| 6,292,701 B1 | 9/2001 | Prass | |
| 6,296,640 B1 * | 10/2001 | Wampler et al. | 606/48 |
| 6,306,100 B1 | 10/2001 | Prass | |
| 6,308,712 B1 | 10/2001 | Shaw | |
| 6,312,392 B1 | 11/2001 | Herzon | |
| 6,319,257 B1 | 11/2001 | Carignan | |
| 6,325,764 B1 | 12/2001 | Griffith | |
| 6,334,068 B1 | 12/2001 | Hacker | |
| 6,348,058 B1 | 2/2002 | Melkent | |
| 6,360,750 B1 | 3/2002 | Gerber | |
| 6,371,968 B1 | 4/2002 | Kogasaka | |
| 6,371,989 B1 | 4/2002 | Chauvin | |
| 6,383,221 B1 | 5/2002 | Scarborough | |
| 6,391,028 B1 * | 5/2002 | Fanton et al. | 606/45 |
| 6,405,733 B1 * | 6/2002 | Fogarty et al. | 128/899 |
| 6,409,766 B1 | 6/2002 | Brett | |
| 6,425,772 B1 | 7/2002 | Bernier | |
| 6,425,859 B1 | 7/2002 | Foley | |
| 6,425,901 B1 | 7/2002 | Zhu | |
| 6,432,140 B1 | 8/2002 | Lin | |
| 6,440,142 B1 | 8/2002 | Ralph | |
| 6,442,814 B1 | 9/2002 | Landry | |
| 6,447,547 B1 | 9/2002 | Michelson | |
| 6,450,952 B1 | 9/2002 | Rioux | |
| 6,451,015 B1 | 9/2002 | Rittman | |
| 6,454,806 B1 | 9/2002 | Cohen | |
| 6,466,817 B1 | 10/2002 | Kaula | |
| 6,468,205 B1 | 10/2002 | Mollenauer | |
| 6,468,207 B1 | 10/2002 | Fowler | |
| 6,468,311 B2 | 10/2002 | Boyd | |
| 6,491,724 B1 | 12/2002 | Ferree | |
| 6,500,128 B2 | 12/2002 | Marino | |
| 6,520,907 B1 | 2/2003 | Foley | |
| 6,524,320 B2 | 2/2003 | DiPoto | |
| 6,527,773 B1 | 3/2003 | Lin | |
| 6,535,759 B1 | 3/2003 | Epstein | |
| D472,634 S | 4/2003 | Anderson | |
| D473,650 S | 4/2003 | Anderson | |
| 6,540,753 B2 * | 4/2003 | Cohen | 606/99 |
| 6,547,823 B2 | 4/2003 | Scarborough | |
| 6,558,423 B1 | 5/2003 | Michelson | |
| 6,564,078 B1 | 5/2003 | Marino | |
| 6,576,017 B2 * | 6/2003 | Foley et al. | 623/17.16 |
| 6,579,244 B2 | 6/2003 | Goodwin | |
| 6,595,998 B2 | 7/2003 | Johnson | |
| 6,620,157 B1 | 9/2003 | Dabney | |
| 6,626,905 B1 | 9/2003 | Schmiel | |
| 6,635,086 B2 | 10/2003 | Lin | |
| 6,641,580 B1 * | 11/2003 | Edwards et al. | 606/41 |
| 6,645,194 B2 | 11/2003 | Briscoe | |
| 6,648,895 B2 * | 11/2003 | Burkus et al. | 606/90 |
| 6,672,019 B1 | 1/2004 | Wenz | |
| 6,676,703 B2 | 1/2004 | Biscup | |
| 6,679,833 B2 | 1/2004 | Smith | |
| 6,706,067 B2 | 3/2004 | Shimp | |
| 6,719,692 B2 | 4/2004 | Kleffner | |
| 6,726,684 B1 * | 4/2004 | Woloszko et al. | 606/32 |
| 6,743,255 B2 | 6/2004 | Ferree | |
| 6,746,484 B1 | 6/2004 | Liu | |
| 6,755,841 B2 | 6/2004 | Fraser | |
| 6,760,616 B2 | 7/2004 | Hoey | |
| 6,761,739 B2 | 7/2004 | Shepard | |
| 6,770,074 B2 | 8/2004 | Michelson | |
| 6,772,012 B2 * | 8/2004 | Woloszko et al. | 607/99 |
| 6,796,985 B2 | 9/2004 | Bolger | |
| 6,810,281 B2 | 10/2004 | Brock | |
| 6,819,956 B2 | 11/2004 | DiLorenzo | |
| 6,821,276 B2 * | 11/2004 | Lambrecht et al. | 606/45 |
| 6,824,564 B2 | 11/2004 | Crozet | |
| 6,847,849 B2 | 1/2005 | Mamo | |
| 6,849,047 B2 | 2/2005 | Goodwin | |
| 6,855,105 B2 | 2/2005 | Jackson | |
| 6,871,099 B1 | 3/2005 | Whitehurst | |
| D503,801 S | 4/2005 | Jackson | |
| 6,902,569 B2 | 6/2005 | Parmer | |
| 6,923,811 B1 * | 8/2005 | Carl et al. | 623/17.11 |
| 6,923,814 B1 * | 8/2005 | Hildebrand et al. | 606/99 |
| 6,926,728 B2 | 8/2005 | Zucherman | |
| 6,929,606 B2 | 8/2005 | Ritland | |
| 6,942,698 B1 * | 9/2005 | Jackson | 623/17.16 |
| 6,945,933 B2 | 9/2005 | Branch | |
| 6,951,538 B2 | 10/2005 | Ritland | |
| 6,964,687 B1 | 11/2005 | Bernard | |
| 6,979,353 B2 | 12/2005 | Bresina | |
| 6,984,245 B2 * | 1/2006 | McGahan et al. | 623/17.11 |
| 6,986,788 B2 | 1/2006 | Paul | |
| 6,989,031 B2 | 1/2006 | Michelson | |
| 7,018,416 B2 | 3/2006 | Hanson | |
| 7,033,394 B2 | 4/2006 | Michelson | |
| 7,047,082 B1 | 5/2006 | Schrom | |
| 7,050,848 B2 | 5/2006 | Hoey | |
| 7,079,883 B2 | 7/2006 | Marino | |
| 7,089,059 B1 | 8/2006 | Pless | |
| D530,423 S | 10/2006 | Miles | |
| 7,118,580 B1 * | 10/2006 | Beyersdorff et al. | 606/99 |
| 7,177,677 B2 | 2/2007 | Kaula | |
| 7,198,598 B2 | 4/2007 | Smith | |
| 7,207,949 B2 * | 4/2007 | Miles et al. | 600/554 |
| 7,226,451 B2 | 6/2007 | Shluzas | |
| 7,261,688 B2 | 8/2007 | Smith | |
| 7,326,248 B2 * | 2/2008 | Michelson | 623/17.11 |
| RE40,156 E * | 3/2008 | Sharps et al. | 606/32 |
| 7,419,505 B2 * | 9/2008 | Fleischmann et al. | 623/17.11 |
| 7,470,236 B1 | 12/2008 | Kelleher | |
| 7,473,222 B2 | 1/2009 | Dewey | |
| 7,481,766 B2 | 1/2009 | Lee | |
| 7,522,953 B2 | 4/2009 | Blewett | |
| 7,556,601 B2 | 7/2009 | Branch | |
| 7,563,286 B2 * | 7/2009 | Gerber et al. | 623/17.14 |
| 7,582,058 B1 | 9/2009 | Miles | |
| 7,643,884 B2 | 1/2010 | Pond | |
| 7,691,057 B2 | 4/2010 | Miles | |
| 7,717,959 B2 | 5/2010 | William | |
| 7,811,325 B2 * | 10/2010 | Cannon et al. | 623/17.14 |
| 7,815,682 B1 | 10/2010 | Peterson | |
| 7,819,801 B2 | 10/2010 | Miles | |
| 7,918,891 B1 | 4/2011 | Curran | |
| 7,935,051 B2 | 5/2011 | Miles | |
| 8,287,597 B1 | 10/2012 | Pimenta | |
| 8,292,815 B2 * | 10/2012 | Burdette et al. | 600/439 |
| 8,673,005 B1 | 3/2014 | Pimenta | |
| 2001/0039949 A1 | 11/2001 | Loubser | |

(56) References Cited

U.S. PATENT DOCUMENTS

| Publication No. | Date | Name | Ref |
|---|---|---|---|
| 2001/0056280 A1 | 12/2001 | Underwood | |
| 2002/0007129 A1 | 1/2002 | Marino | |
| 2002/0010392 A1 | 1/2002 | Desai | |
| 2002/0045922 A1* | 4/2002 | Nield et al. | 607/89 |
| 2002/0058950 A1 | 5/2002 | Winterbottom | |
| 2002/0072686 A1 | 6/2002 | Hoey | |
| 2002/0077632 A1* | 6/2002 | Tsou | 606/90 |
| 2002/0123780 A1 | 9/2002 | Grill | |
| 2002/0161415 A1 | 10/2002 | Cohen | |
| 2002/0193843 A1 | 12/2002 | Hill | |
| 2003/0032966 A1 | 2/2003 | Foley | |
| 2003/0100950 A1 | 5/2003 | Moret | |
| 2003/0105503 A1 | 6/2003 | Marino | |
| 2003/0105528 A1 | 6/2003 | Shimp | |
| 2003/0130737 A1* | 7/2003 | McGahan et al. | 623/17.11 |
| 2003/0139648 A1 | 7/2003 | Foley | |
| 2003/0139812 A1 | 7/2003 | Garcia | |
| 2003/0149341 A1 | 8/2003 | Clifton | |
| 2003/0171813 A1* | 9/2003 | Kiester | 623/17.11 |
| 2003/0225405 A1 | 12/2003 | Weiner | |
| 2003/0236544 A1 | 12/2003 | Lunsford | |
| 2004/0024400 A1* | 2/2004 | Michelson | 606/41 |
| 2004/0127893 A1* | 7/2004 | Hovda | 606/15 |
| 2004/0153155 A1 | 8/2004 | Chung | |
| 2004/0199084 A1 | 10/2004 | Kelleher | |
| 2004/0225228 A1 | 11/2004 | Ferree | |
| 2005/0004593 A1 | 1/2005 | Simonson | |
| 2005/0004623 A1 | 1/2005 | Miles | |
| 2005/0033380 A1 | 2/2005 | Tanner | |
| 2005/0075578 A1 | 4/2005 | Gharib | |
| 2005/0080320 A1 | 4/2005 | Lee | |
| 2005/0149011 A1* | 7/2005 | Ashley et al. | 606/41 |
| 2005/0149035 A1 | 7/2005 | Pimenta | |
| 2005/0182454 A1 | 8/2005 | Gharib | |
| 2005/0192575 A1 | 9/2005 | Pacheco | |
| 2005/0197702 A1* | 9/2005 | Coppes et al. | 623/17.12 |
| 2005/0273093 A1* | 12/2005 | Patel et al. | 606/41 |
| 2006/0025703 A1 | 2/2006 | Miles | |
| 2006/0052828 A1 | 3/2006 | Kim | |
| 2006/0069315 A1 | 3/2006 | Miles | |
| 2006/0089633 A1* | 4/2006 | L. Bleich et al. | 606/32 |
| 2006/0089640 A1* | 4/2006 | Bleich et al. | 606/45 |
| 2006/0129244 A1 | 6/2006 | Ensign | |
| 2006/0224078 A1 | 10/2006 | Hoey | |
| 2006/0235426 A1* | 10/2006 | Lim et al. | 606/99 |
| 2007/0016097 A1 | 1/2007 | Farquhar | |
| 2007/0072475 A1* | 3/2007 | Justin et al. | 439/354 |
| 2007/0088441 A1* | 4/2007 | Duggal et al. | 623/17.16 |
| 2007/0191945 A1 | 8/2007 | Yu | |
| 2007/0198062 A1 | 8/2007 | Miles | |
| 2007/0270972 A1 | 11/2007 | Gordon | |
| 2007/0293782 A1 | 12/2007 | Marino | |
| 2008/0015582 A1* | 1/2008 | DiPoto et al. | 606/61 |
| 2008/0033436 A1* | 2/2008 | Song et al. | 606/61 |
| 2008/0058606 A1 | 3/2008 | Miles | |
| 2008/0064976 A1 | 3/2008 | Kelleher | |
| 2008/0064977 A1 | 3/2008 | Kelleher | |
| 2008/0065178 A1 | 3/2008 | Kelleher | |
| 2008/0071191 A1 | 3/2008 | Kelleher | |
| 2008/0097164 A1 | 4/2008 | Miles | |
| 2008/0103504 A1* | 5/2008 | Schmitz et al. | 606/79 |
| 2008/0147194 A1 | 6/2008 | Grotz | |
| 2008/0262583 A1* | 10/2008 | Sharkey et al. | 607/117 |
| 2008/0287947 A1* | 11/2008 | Ellman et al. | 606/45 |
| 2008/0287957 A1* | 11/2008 | Hester et al. | 606/99 |
| 2008/0300465 A1 | 12/2008 | Feigenwinter | |
| 2009/0062917 A1 | 3/2009 | Foley | |
| 2009/0076616 A1* | 3/2009 | Duggal et al. | 623/17.16 |
| 2009/0124860 A1 | 5/2009 | Miles | |
| 2009/0138050 A1 | 5/2009 | Ferree | |
| 2009/0192403 A1 | 7/2009 | Gharib | |
| 2009/0204016 A1 | 8/2009 | Gharib | |
| 2009/0306717 A1* | 12/2009 | Kercher et al. | 606/258 |
| 2010/0023006 A1* | 1/2010 | Ellman | 606/45 |
| 2010/0069783 A1 | 3/2010 | Miles | |
| 2010/0130827 A1 | 5/2010 | Pimenta | |
| 2010/0152603 A1 | 6/2010 | Miles | |
| 2010/0152853 A1 | 6/2010 | Kirschman | |
| 2010/0160738 A1 | 6/2010 | Miles | |
| 2010/0174148 A1 | 7/2010 | Miles | |
| 2010/0204693 A1* | 8/2010 | Sanders et al. | 606/41 |
| 2010/0324553 A1* | 12/2010 | Sharps et al. | 606/41 |
| 2011/0146692 A1* | 6/2011 | Callaghan et al. | 128/831 |
| 2011/0166657 A1 | 7/2011 | Thalgott | |
| 2011/0208309 A1 | 8/2011 | Peterson | |
| 2011/0245819 A1* | 10/2011 | Nardini et al. | 606/13 |
| 2012/0116397 A1* | 5/2012 | Rencher et al. | 606/45 |
| 2012/0203348 A1* | 8/2012 | Michelson | 623/17.16 |
| 2012/0232552 A1* | 9/2012 | Morgenstern Lopez et al. | 606/45 |
| 2013/0096683 A1 | 4/2013 | Kube | |

FOREIGN PATENT DOCUMENTS

| | | |
|---|---|---|
| EP | 0369603 | 5/1990 |
| EP | 0667127 A1 | 8/1995 |
| EP | 0706876 | 4/1996 |
| EP | 0517030 B1 | 9/1996 |
| EP | 0796593 | 9/1997 |
| EP | 0809974 | 12/1997 |
| EP | 0809975 A3 | 4/1998 |
| EP | 0880938 | 12/1998 |
| EP | 0972538 | 1/2000 |
| EP | 0811356 | 7/2002 |
| FR | 2795624 | 1/2001 |
| WO | WO-9000037 | 1/1990 |
| WO | WO-9106261 | 5/1991 |
| WO | WO-9214423 | 9/1992 |
| WO | WO-9404100 | 3/1994 |
| WO | WO-9410928 | 5/1994 |
| WO | WO-9501810 | 1/1995 |
| WO | WO-9608205 | 3/1996 |
| WO | WO-9617564 | 6/1996 |
| WO | WO-9641582 | 12/1996 |
| WO | WO-9720513 | 6/1997 |
| WO | WO-9733525 | 9/1997 |
| WO | WO-9737620 | 10/1997 |
| WO | WO-9809586 | 3/1998 |
| WO | WO-9814142 | 4/1998 |
| WO | WO-9817208 | 4/1998 |
| WO | WO-9825539 | 6/1998 |
| WO | WO-9908627 | 2/1999 |
| WO | WO-9938461 | 8/1999 |
| WO | WO-0038754 | 7/2000 |
| WO | WO-0045712 | 8/2000 |
| WO | WO-0045713 | 8/2000 |
| WO | WO-0066217 | 11/2000 |
| WO | WO-0067645 | 11/2000 |
| WO | WO-0141681 | 6/2001 |
| WO | WO-0149333 | 12/2001 |
| WO | WO-02054960 | 7/2002 |
| WO | WO-0137728 | 8/2002 |
| WO | WO-03005887 | 1/2003 |
| WO | WO-03026482 | 5/2004 |
| WO | WO-03037170 | 12/2004 |
| WO | WO-2005013805 | 2/2005 |
| WO | WO-2005030318 | 4/2005 |
| WO | WO-2006042241 | 4/2006 |
| WO | WO-2006066217 | 6/2006 |

OTHER PUBLICATIONS

"510(k) Premarket Notification INS-1 Intraoperative Nerve Surveillance System: Section IV Device Description", (Sep. 25, 2003), 12-51.

"510(k) Premarket Notification: Guided Spinal Arthroscopy System (Device Description)", NuVasive Letter, (Feb. 1, 1999), 40 pgs.

"510(k) Premarket Notification: Neurovision JJB System (Device Description)", NuVasive Letter , (Jun. 24, 2005), 16 pgs.

"510(k) Premarket Notification: Neurovision JJB System (Device Description)", NuVasive Letter, (Jun. 24, 2005), 16 pgs.

"510(k) Premarket Notification: Spinal System (Summary)", (Apr. 12, 2004), 10 pgs.

(56) References Cited

OTHER PUBLICATIONS

"510(k) Summary NIM Monitor", (Sep. 4, 1998), 4 pgs.
"510k Guided Arthroscopy System", (Oct. 5, 1999), 6 pgs.
"510k INS-1 Intraoperative Nerve Surveillance System", (Nov. 13, 2000), 7 pgs.
"510k Neuro Vision JIB System", NuVasive Letter, (Oct. 16, 2001), 5 pgs.
"Anatomy of the Lumbar Spine in MED TM MicroEndoscopic Discectomy", 1997, 14 pgs.
Anderson, "Pedicle screws with high electrical resistance: a potential source of error with stimulus-evoked EMG", Spine, 27(14), (Jul. 15, 2002), 1577-1581.
Baulot, "Complementary anterior spondylodesis by thoracoscopy. Technical note regarding an observation", Lyon Surg, 90(5), (1994), 347-351.
Bergey, "Endoscopic Lateral Transpsoas Approach to the Lumbar Spine", Spine, 29(15), (2004), 1681-1688.
Berry, "A morphometric study of human lumbar and selected thoracic vertebrae, study of selected vertebrae", Spine, 12(4), (1996), 362-367.
Bose, "Neurophysiologic Monitoring of Spinal Nerve Root Function During Instrumented Posterior Lumber Spine Surgery", Spine, 27(13),(2002), 1444-1450.
"Brackmann II EMG System", Medical Electronics, (1999), 4 pgs.
Brau *, "Chapter 22: Anterior Retroperitoneal Muscle-Sparing approach to L2-S1 of the Lumbar Spine", Surgical Approaches to the Spine, (2003), 165-181.
Calancie *, "Stimulus-Evoked EMG Monitoring During Transpedicular Lumbosacral Spine Instrumentation", Spine, 19(24), (1994), 2780-2786.
Clements *, "Evoked and Spontaneous Electromyography to Evaluate Lumbosacral Pedicle Screw Placement", Spine, 21(5), (1996), 600-604.
"CoRoent.RTM. XL & XLR Marketing Brochure (9004225 B.0)", NuVasive Inc., (2006), 2 pgs.
"CoRoent.RTM. XL & XLR Marketing Brochure (9004225 C.0)", NuVasive Inc., (2007), 2pgs.
"CoRoent.TM. Marketing Brochure (9004001 A.0)", NuVasive Inc, (2004), 2 pgs.
"CoRoent.TM. Marketing Brochure (9004001 C.0)", NuVasive Inc, (2005), 2 pgs.
Crock H.V., "A Short Practice of Spinal Surgery", Second, Revised Edition, (1993).
Crock H.V., "Anterior Lumbar Interbody Fusion," Clinical Orthopaedics and Related Research, No. One Hundred Sixty Five, (1982), 157-163.
Danesh-Clough, "The Use of Evoked EMG in Detecting Misplaced Thoracolumbar Pedicle Screws", Spine, 26(12), (Jun. 15, 2001), 1313-1316.
Darden, "A Comparison of Impedance and Electromyogram Measurements in Detecting the Presence of Pedicle Wall Breakthrough", Spine, 23(2), (Jan. 15, 1988), 256-262.
Dezawa, "Retroperitoneal Laparoscopic Lateral Approach to the Lumbar Spine: A New Approach, Technique, and Clinical Trial", Journal of Spinal Disorders, 13(2), (2000), 138-143.
Dirksmeier, "Microendoscopic and Open Laminotomy and Discectomy in Lumbar Disc Disease", Seminars in Spine Surgery, 11 (2), (1999), 138-146.
Ebraham, "Anatomic Relations Between the Lumbar Pedicle and the Adjacent Neural Structures,", Spine, 22(20), (Oct. 15, 1997), 2338-2341.
"Epoch 2000 Neurological Workstation,", Axon 501(k) Notification, (Dec. 3, 1997), 464 pgs.
Foley, "Microendoscopic Discectomy", Techniques in Neurosurgery,3(4), 301-307.
Ford, "Anatomic Relations Between the Lumbar Pedicle and the Adjacent Neural Structures,", Spine, 9, (1984), 73-77.
Friedman, "Percutaneous discectomy: An alternative to chemonucleolysis ", Neurosurgery, 13 (5), (1983), 542-547.
Gardocki, "Tubular diskectomy minimizes collateral damage: A logical progression moves spine surgery forward", AAOS Now, (2009), 5 pgs.
Glassman, "A Prospective Analysis of Intraoperative Electromyographic Monitoring of Pedicle Screw Placement with Computed Tomographic Scan Confirmation", Spine, 20(12), (1995), 1375-1379.
Greenblatt, "Needle Nerve Stimulator-Locator: Nerve Blocks with a New Instrument for Locating Nerves", Anesthesia & Analgesia, 41(5), (1962), 599-602.
Haig, "Point of view", Spine, 27(24), (2002), 2819.
Haig, "The Relation Among Spinal Geometry on MRI, Paraspinal Electromyographic Abnormalities, and Age in Persons Referred for Electrodiagnostic Testing of Low Back Symptoms", Spine, 27(17), (Sep. 1, 2002), 1918-1925.
Holland, "Higher Electrical Stimulus Intensities are Required to Activate Chronically Compressed Nerve Roots: Implications for Intraoperative Electromyographic Pedicle Screw Testing,", Spine, 23(2), (Jan. 15, 1998), 224-227.
Holland, "Intraoperative Electromyography During Thoracolumbar Spinal Surgery", Spine, 23(17), (1998), 1915-1922.
Hovorka, "Five years' experience of retroperitoneal lumbar and thoracolumbar surgery", Eur. Spine J., 9(1), (2000), S30-S34.
"INS-1 Screw Test", 2001, 10 pgs.
International Application Serial No. PCT/US00/32329, International Search Report mailed Apr. 27, 2001, 9 pgs.
International Application Serial No. PCT/US01/18579, International Search Report mailed Jan. 15, 2002, 6 pgs.
International Application Serial No. PCT/US01/18606, International Search Report mailed Oct. 18, 2001, 6 pgs.
International Application Serial No. PCT/US02/22247, International Search Report mailed Mar. 27, 2003, 4 pgs.
International Application Serial No. PCT/US02/30617, International Search Report mailed Jun. 5, 2003, 4 pgs.
International Application Serial No. PCT/US02/35047, International Search Report mailed Aug. 11, 2003, 5 pgs.
International Application Serial No. PCT/US03/02056, International Search Report mailed Aug. 12, 2003, 5 pgs.
Isley, "Recent Advances in Intraoperative Neuromonitoring of Spinal Cord Function: Pedicle Screw Stimulation Techniques", American Journal of Electroneurodagnostic Technology, (Jun. 1, 1997), 93-126.
Japanese Application Serial No. 2006-528306, Office Action mailed Jun. 10, 2009, 4 pgs.
Journee, "System for Intra-Operative Monitoring of the Cortical Integrity of the Pedicle During Pedicle Screw Placement in Low-Back Surgery: Design and Clinical Results", Sensory and Neuromuscular Diagnostic Instrumentation and Data Analysis I, 18th Annual International Conference on Engineering in Medicine and Biology Society, (1998), 144-145.
Kemp, H.B.S, "Anterior fusion of the spine for infective lesions in adults", Journal of Bone & Joint Surgery, 715-734.
Kossman, "Minimally Invasive Vertebral Replacement with Cages in Thoracic and Lumbar Spine", European Journal of Trauma, 27, (2001), 292-300.
Kossman, "The use of a retractor system (SynFrame) for open, minimal invasive reconstruction of the anterior column of the thoracic and lumbar spine", Eur Spine J., 10, (2001), 396-402.
Larson, "Surgery of the Lumbar Spine", Thieme Medical Publishers, Inc, (1999), 305-319.
Lenke, "Triggered Electromyographic Threshold for Accuracy of Pedicle Screw Placement", Spine, 20(4), (1995), 1585-1591.
Maguire, "Evaluation of Intrapedicular Screw Position Using Intraoperative Evoked Electromyography", Spine, 20(90), (1995), 1068-1074.
Marina, "New Technology for Guided Navigation with Real Time Nerve Surveillance for Minimally Invasive Spine Discectomy & Arthrodesis", Spineline, (2000), p. 39.
Martin, "Initiation of Erection and Semen Release by Rectal Probe Electrostimulation (RPE", The Journal of Urology, 129, (1983), 637-642.
Mathews, "Laparoscopic Discectomy with Anterior Lumbar Interbody Fusion", SPINE,20(16), (1995), 1797-1802.

(56) References Cited

OTHER PUBLICATIONS

Mayer, "A New Microsurgical Technique for Minimally Invasive Anterior Lumbar Interbody Fusion", Spine, 22(6), (1997), 691-699.
Mayer, "Microsurgical Anterior Approaches to the Lumbar Spine for Interbody Fusion and Total Disc Replacement", Neurosurgery, 51(2), (2002), 159-165.
Mayer, "The ALIF Concept", Eur Spine J., 9 (1), (2000), S35-S43.
McFee, "Minimally Invasive Anterior Retroperitoneal Approach to the Lumbar Spine: Emphasis on the Lateral BAK", Spine, 23(13), (1998), 1476-1484.
"METRx Delivered Order Form", Medtronic Sofamor Danek, (1999), 13 pgs.
"MetRx System MicroEndoscopic Discectomy: An Evolution in Minimally Invasive Spine Surgery", Sofamor Danek,(1999), 6 pgs.
"METRx System Surgical Technique", Medtronic Sofamor Danek, (2004), 22 pgs.
"METRx.TM. MicroDisectomy System", Medtronic Sofamor Danek USA, (2000), 21 pgs.
Minahan, "The Effect of Neuromuscular Blockade on Pedicle Screw Stimulation Thresholds", Spine, 25(19), (Oct. 1, 2000), 2526-2530.
"Neurovision SE Nerve Locator/Monitor", RLN Systems Inc. Operators Manual, (1999), 22 pgs.
"NIM-Response Nerve Integrity Monitor Intraoperative EMG Monitor User's Guide, Revision B", Medtronic XOMED Surgical Products, Inc, (2000), 47 pgs.
"NuVasive Triad.TM. Cortical Bone Allograft", 2000, (Sep. 25, 2003), 1 pg.
"NuVasive Triad.TM. Tri-Columnar Spinal EndoArthrodesis TM", Minimally Invasive Guidance, 2000, (Sep. 25, 2003), 1 pg.
"NuVasive Vector TM Cannulae", 2000, 1 pg.
"NuVasive's spine surgery system cleared in the US", Pharm & Medical Industry Week, (Dec. 10, 2001), 1 pg.
"NuVasiveTM Receives Clearance to Market Two Key Elem Minimally Invasive Spine Surgery System", (Nov. 27, 2001), 20 pgs.
"Percutaneous endoscopic discectomy: surgical technique and preliminary results compared to microsurgical discectomy", J. Neurosurg., 78, 1993, 216-225.
Pimenta, "Implante de protese de nucleo pulpost: analise inicial", Journal Brasileiro de Neurocirurgia, 12(2), (2001), 93-96.
Pimenta, "Initial Clinical Results of Direct Lateral, Minimally Invasive Access to the Lumbar Spine for Disc Nucleus Replacement Using a Novel Neurophysiological Monitoring System", The 9 Sup IMAST, (May 1, 2002), 1 pg.
Pimenta, "The Lateral Endoscopic Transpsoas Retroperitoneal Approach (Letra) for Implants in the Lumbar Spine", World Spine II—Second Interdisciplinary Congress on Spine Care, (2003), 2 pgs.
Pither, "The Use of Peripheral Nerve Stimulators for Regional Anesthesia: Review of Experimental Characteristics Technique and Clinical Applications", Regional Anesthesia, 10, (1985), 49-58.
"Premarket Notification: Neurovision JJB System (Device Description)", NuVasive Letter, (Aug. 20, 2007), 8 pgs.
Raj, "Infraclavicular Brachial Plexus Block—A New Approach", Anesthesia and Analgesia, (52)6, (1973), 897-904.
Raj, "The Use of Peripheral Nerve Stimulators for Regional Anesthesia", Clinical Issues in Regional Anesthesia, 1(4), (1985), 1-6.
Raj, "Use of the Nerve Stimulator for Peripheral Blocks", Regional Anesthesia, (1980), 14-21.
Rao, "Dynamic retraction of the psoas muscle to expose the lumbar spine using the retroperitoneal approach", J. Neurosurg Spine, 5, (2006), 468-470.
Raymond, "The Nerve Seeker: A System for Automated Nerve Localization", Regional Anesthesia,17(3), (1992), 151-162.
Rose, "Persistently Electrified Pedicle Stimulation Instruments in Spinal Instrumentation: Techniques and Protocol Development", SPINE, 22(3), (1997), 334-343.
Schaffer, "Percutaneous Posterolateral Lumbar Discectomy and Decompression with a 6.9-Millimeter Cannula", The Journal of Bone and Joint Surgery, 73A(6), (1991), 822-831.
Schick, "Microendoscopic lumbar discectomy versus open surgery: an intraoperative EMG study", Eur Spine J, 11, (2002), 20-26.
Shafik, "Cavernous Nerve Simulation through an Extrapelvic Subpubic Approach: Role in Penile Erection", Eur. Urol, 26, (1994), 98-102.
Smith, "MetRx System MicroEndoscopic Discectomy: Surgical Technique", Medtronic Sofamor Danek, (2000), 24 pgs.
"Special 510(k) Premarket Notification: Neurovision JJB System (Device Description)", NuVasive Letter, (Mar. 1, 2004), 16 pgs.
"Special 510(k) Premarket Notification: Neurovision JJB System (Device Description)", NuVasive Letter, (May 26, 2005), 17 pgs.
"Special 510(k) Premarket Notification: Neurovision JJB System (Device Description)", NuVasive Letter, (Jul. 3, 2003), 18 pgs.
"Special 510(k) Premarket Notification: Neurovision JJB System (Device Description)", NuVasive Letter, (Sep. 14, 2006), 17 pgs.
"The Brackmann II EMG Monitoring System", Medical Electronics Co. Operator's Manual Version 1.1, (1995), 50 pgs.
"The Nicolet Viking IV", Nicolet Biomedical Products, (1999), 6 pgs.
Toleikis, "The Usefulness of Electrical Stimulation for Assessing Pedicle Screw Replacements", Journal of Spinal Disorder, 12(4), (2000), 283-289.
Traynelis, "Spinal Arthroplasty", Neurological Focus, 13(2), (2002), 12 pgs.
"UNION.TM. /UNION-L.TM. Anterior & Lateral Impacted Fusion Devices: Surgical Technique", Medtronic Sofamor Danek, (2001), 20 pgs.
"Vector.TM.", Cannulae, 2001, 1 pg.
"Vertebral Body Access System", 2000, 1 pg.
Wolfa, "Retroperitoneal lateral lumbar interbody fusion with titanium threaded fusion cages", J. Neurosurg (Spine 1), 96, (2002), 50-55.
Zdeblick, Thomas A, "Anterior Approaches to the Spine", (1999), 43 pgs.
Final Written Decision from IPR 2013-00506, dated Feb. 11, 2015, 25 pages.
Final Written Decision from IPR 2013-00507, dated Feb. 11, 2015, 14 pages.
Final Written Decision from IPR 2013-00508, dated Feb. 11, 2015, 19 pages.
Final Written Decision from IPR 2014-00034, dated Apr. 3, 2015, 48 pages.
Final Written Decision from IPR 2014-00073, dated Apr. 3, 2015, 36 pages.
Final Written Decision from IPR 2014-00074, dated Apr. 3, 2015, 31 pages.
Final Written Decision from IPR 2014-00075, dated Apr. 3, 2015, 39 pages.
Final Written Decision from IPR 2014-00081, dated Apr. 3, 2015, 44 pages.
Final Written Decision from IPR 2014-00087, dated Apr. 3, 2015, 36 pages.

\* cited by examiner

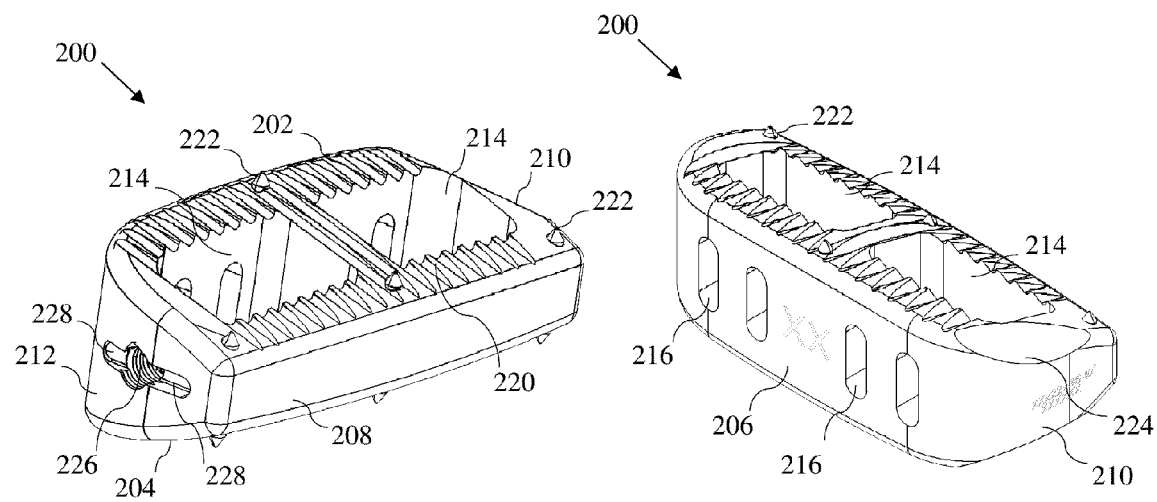
FIG. 24
FIG. 25
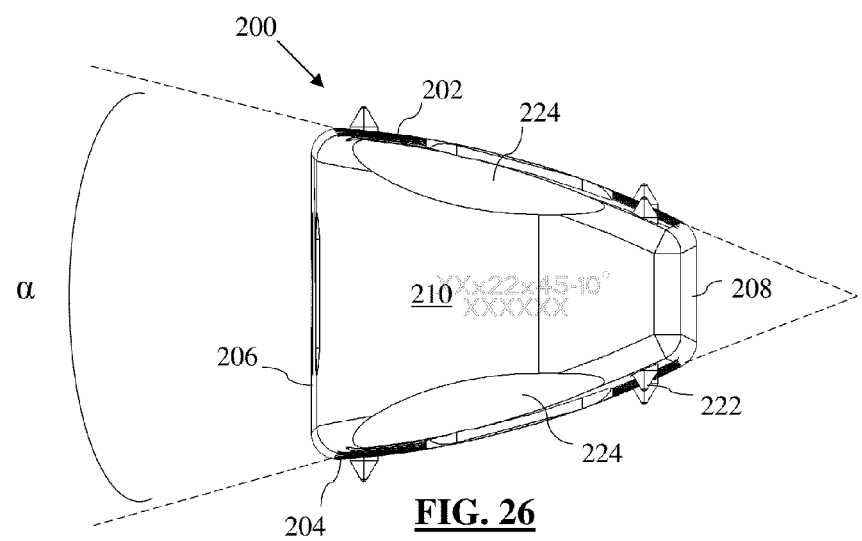
FIG. 26

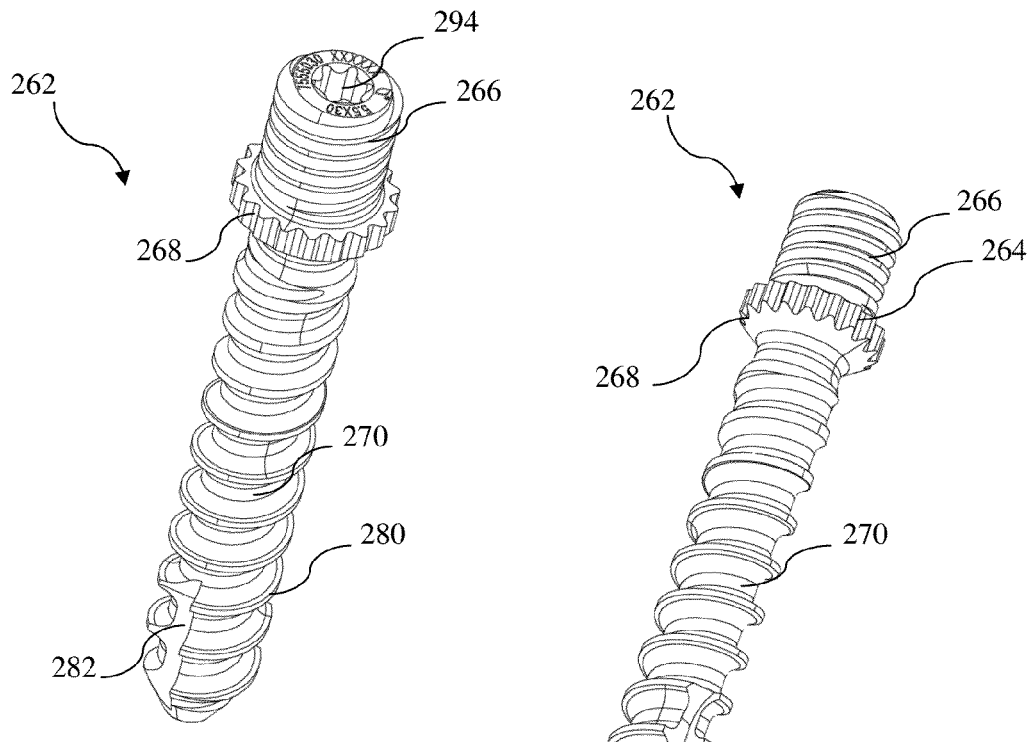
FIG. 36
FIG. 37
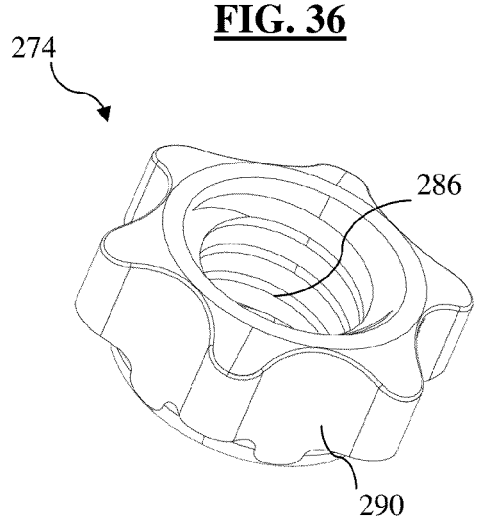
FIG. 38
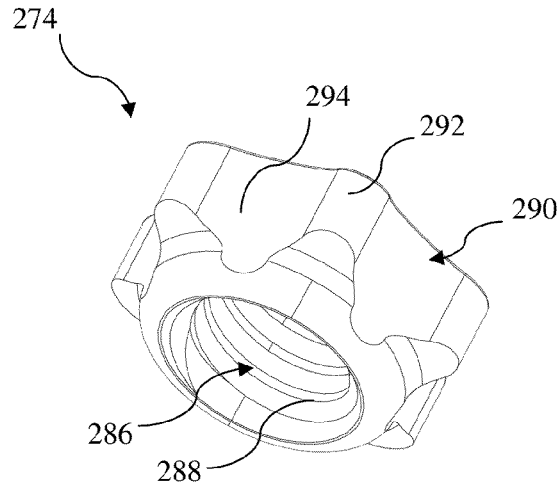
FIG. 39

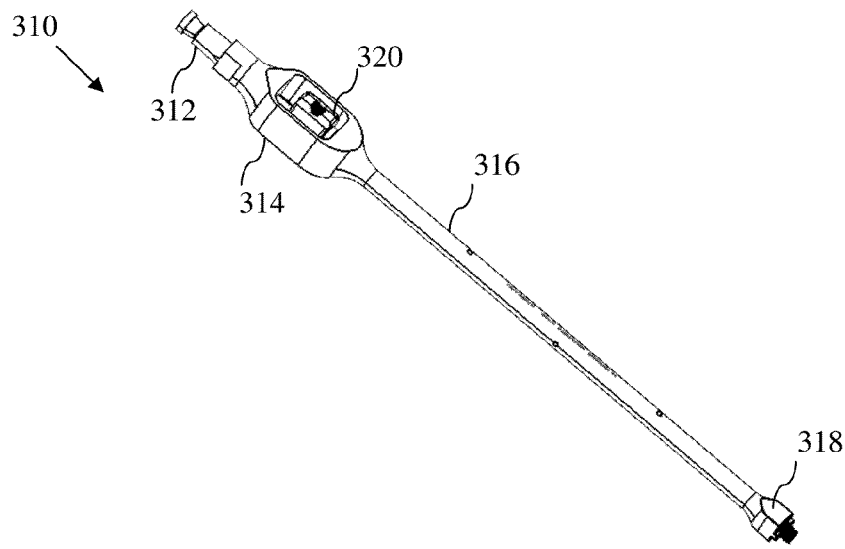
FIG. 49
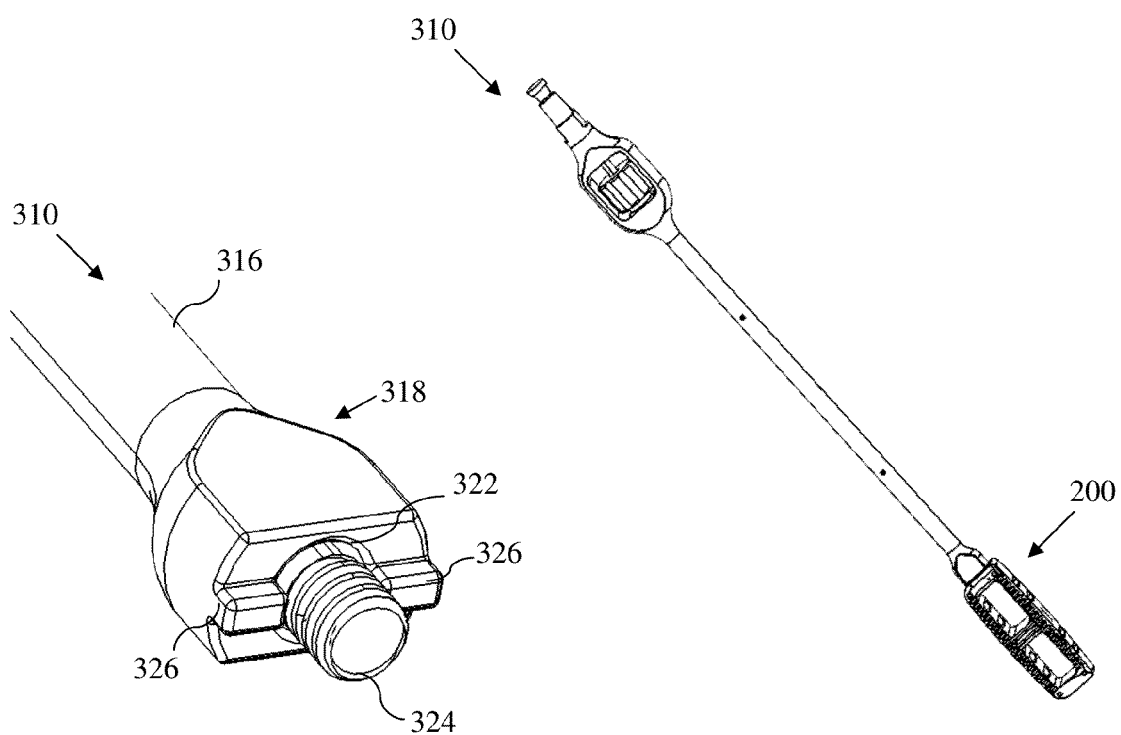
FIG. 50      FIG. 51

METHOD AND APPARATUS FOR PERFORMING SPINE SURGERY

CROSS-REFERENCE TO RELATED APPLICATIONS

This application is a continuation-in-part of U.S. application Ser. No. 12/799,021, now U.S. Pat. No. 8,287,597, filed on Apr. 16, 2010, which claims the benefit of U.S. Provisional Application Ser. No. 61/212,921, filed Apr. 16, 2009 and U.S. Provisional Application Ser. No. 61/319,823, filed Mar. 31, 2010, the entire contents of which are all hereby expressly incorporated by reference into this disclosure as if set forth in its entirety herein. The present application also claims the benefit of priority from U.S. Provisional Patent Application Ser. No. 61/319,823, filed on Mar. 31, 2010 and U.S. Provisional Application Ser. No. 61/357,951, filed on Jun. 23, 2010, the entire contents of which are each hereby expressly incorporated by reference into this disclosure as if set forth in its entirety herein.

FIELD

The present invention relates to implants, tools, and methods for adjusting sagittal imbalance of a spine.

BACKGROUND

A human spine has three main regions—the cervical, thoracic, and lumbar regions. In a normal spine, the cervical and lumbar regions have a lordotic (backward) curvature, while the thoracic region has a kyphotic (forward) curvature. Such a disposition of the curvatures gives a normal spine an S-shape. Sagittal imbalance is a condition in which the normal alignment of the spine is disrupted in the sagittal plane causing a deformation of the spinal curvature. One example of such a deformity is "flat-back" syndrome, wherein the lumbar region of the spine is generally linear rather than curved. A more extreme example has the lumbar region of the spine exhibiting a kyphotic curvature such that the spine has an overall C-shape, rather than an S-shape. Sagittal imbalance is disadvantageous from a biomechanical standpoint and generally results in discomfort, pain, and an awkward appearance in that the patient tends to be bent forward excessively.

Various treatments for sagittal imbalance are known in the art. These treatments generally involve removing at least some bone from a vertebra (osteotomy) and sometimes removal of the entire vertebra (vertebrectomy) in order to reduce the posterior height of the spine in the affected region and recreate the lordotic curve. Such procedures are traditionally performed via an open, posterior approach involving a large incision (often to expose multiple spinal levels at the same time) and require stripping of the muscle tissue away from the bone. These procedures can have the disadvantages of a large amount of blood loss, high risk, long operating times, and a long and painful recovery for the patient.

In some other treatments, achieving sagittal balance is accomplished by via an open, anterior approach to position an intervertebral implant between two affected vertebrae in order to increase the anterior height of the spine in the affected region and thereby recreate the lordotic curve. Effectuating an anterior spinal fusion typically involves retracting the great vessels (aorta and vena cava) and tissue adjacent to the anterior longitudinal ligament (ALL), then severing the ALL 16 to increase flexibility and permit insertion of the implant between the adjacent vertebrae. The anterior approach is advantageous in that the ALL 16 is generally exposed, allowing the physician to simply dissect across the exposed portion of the ALL 16 to access the spine. The anterior approach to the spine can also have the disadvantages of a large amount of blood loss, build-up of scar tissue near vital organs, and sexual dysfunction in males. Furthermore, depending upon the patient, multiple procedures, involving both anterior and posterior approaches to the spine, may be required.

In contrast, a lateral approach could be used to access a target spinal site, remove the intervertebral disc between two affected vertebrae, and insert an intervertebral implant. A lateral approach to the spine provides a number of advantages over the posterior and anterior approaches to the spine. Because a lateral approach may be performed without creating a large incision or stripping muscle from bone, this approach does not present the problems associated with a posterior approach, namely there is no large incision, muscle stripping, high blood loss, long operating time, or long and painful recovery for the patient. Furthermore, because a lateral approach to the spine does not involve exposing the anterior aspect of the ALL 16, retracting the great vessels and nearby tissues is unnecessary such that the risks of blood loss, scar tissue, and sexual dysfunction are much less likely to be encountered.

However, in patients with sagittal imbalance, release of the ALL 16 may be necessary to achieve the flexibility between the two affected vertebrae to facilitate insertion of an implant and achieve the amount of correction desired. A need exists for implants, tools, and methods for safe and reproducible means of releasing the ALL 16 via lateral approach as well as restoring the lordotic curvature of the lumbar spine. The present invention is directed at overcoming, or at least improving upon, the disadvantages of the prior art.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 24 is a posterior side perspective view of a hyper-lordotic implant according to a first example embodiment;

FIG. 25 is an anteriorside perspective view of the hyper-lordotic implant of FIG. 24;

FIG. 26 is a lateral side view of the hyper-lordotic implant of FIG. 24;

FIGS. 36 and 37 are perspective views of an example anchor for securing the position of the hyper-lordotic implant of FIG. 34;

FIGS. 38 and 39 are perspective views of an example locking element for securing the anchor of FIGS. 36 and 37 to the implant of FIG. 34;

FIG. 49 is a perspective view of an insertion instrument for implanting the hyper-lordotic implants, according to one example embodiment;

FIG. 50 is an enlarged perspective view of the distal head of the insertion instrument of FIG. 49;

FIG. 51 is a perspective view of the insertion instrument of FIG. 49 coupled to the hyper-lordotic implant of FIG. 24;

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The methods and devices described herein include a variety of inventive features and components that warrant patent protection, both individually and in combination.

Figure 1:
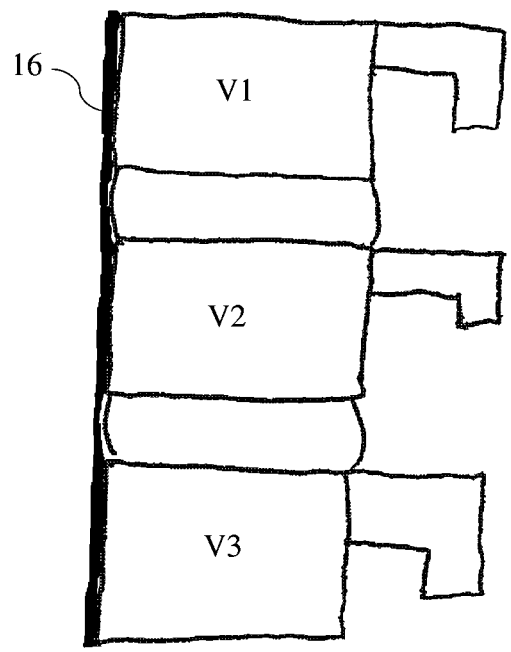
FIG. 1 is a lateral view representing a portion of a sagitally imbalanced lumbar spine lacking the normal lordotic curvature.
Figure 2:
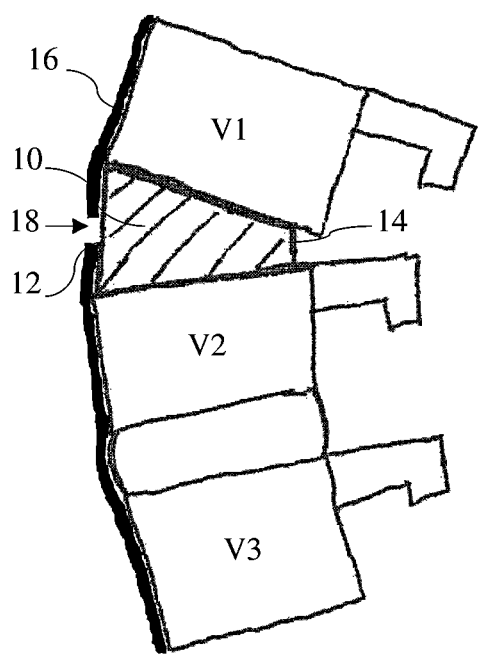
FIG. 2 is a lateral view representing the lumbar spine of FIG. 1 after restoration of the lordotic curvature using a hyper-lordotic fusion implant, according to one example embodiment.

With reference to FIGS. 1-2, devices and methods described herein are utilized to correct sagittal imbalance, including lumbar kyphosis, by increasing the anterior height of the affected spinal area (as opposed to reducing the posterior height, for example via a pedicle subtraction osteotomy). FIG. 1 illustrates a portion of the lumbar spine lacking the standard lordotic curvature. To correct the sagittal imbalance, illustrated in FIG. 2, a hyper-lordotic implant 10 is positioned into the disc space at the appropriate spinal level (e.g. between V1 and V2). An anterior sidewall 12 of hyper-lordotic implant 10 has a height significantly larger than an opposing posterior sidewall 14 such that when the implant is positioned within the disc space the anterior aspects of V1 and V2 are forced apart while the posterior aspects are not (or at least not to the same degree), thus imparting a lordotic curvature into the spine. To allow the anterior aspects of V1 and V2 to separate and receive the hyper-lordotic implant 10, the anterior longitudinal ligament (ALL) 16 that runs along the anterior aspect of the spine may be released or cut 18. Releasing the ALL provides greater flexibility of movement between the adjacent vertebral bodies, which allows for a larger height implant and provides greater opportunity to establish or re-establish a generally normal lordotic curvature in the lumbar region of the spine.

According to a preferred method, the implant 10 is implanted through a lateral access corridor formed through the side of the patient. Accessing the targeted spinal site through the lateral access corridor avoids a number of disadvantages associated with posterior access (e.g. cutting through back musculature and possible need to reduce or cut away part of the posterior bony structures like lamina, facets, and spinous process) and anterior access (e.g. use of an access surgeon to move various organs and blood vessels out of the way in order to reach the target site). Accordingly, by accessing the target site via a lateral access approach and correcting the sagittal imbalance without reducing the posterior height (i.e. no bone removal) the high blood loss and painful recovery associated previous methods may be avoided (or at least mitigated).

Figure 3:
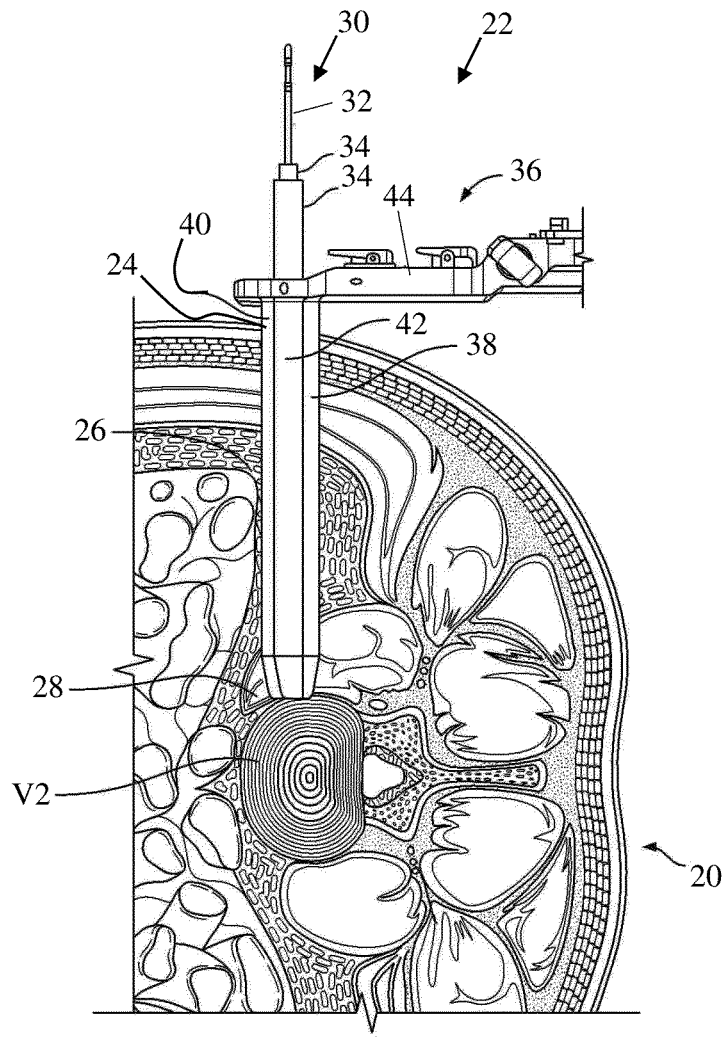
FIG. 3 is a top-down view depicting the creation of a lateral access corridor formed with a surgical access system via a lateral approach through the side of the patient to the target disc space, according to one example embodiment.
Figure 4:
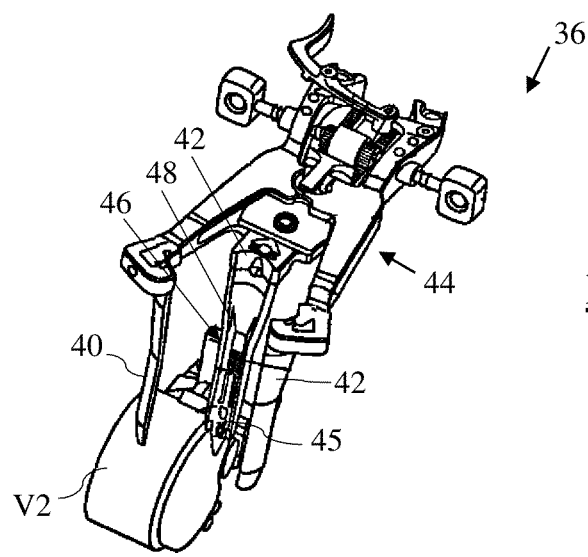
FIG. 4 is a perspective view depicting a lateral access corridor formed with a retractor assembly through the side of the patient to the target disc space, according to one example embodiment.

According to one example, the lateral access approach to the targeted spinal space may be performed according to the instruments and methods described in commonly owned U.S. Pat. No. 7,207,949 entitled "Surgical Access System and Related Methods," and/or U.S. Pat. No. 7,905,840 entitled "Surgical Access System and Related Methods," the entire contents of which are each incorporated herein by reference as if set forth herein in their entireties. With reference to FIGS. 3-4, a discussion of the lateral access instruments and methods is provided in brief detail. With the patient 20 positioned on his side, a surgical access system 22 is advanced through an incision 24, into the retroperitoneal space 26, and then through the psoas muscle 28 until the targeted spinal site (e.g. the disc space between V1 and V2) is reached. The access system 22 may include at least one tissue dilator, and preferably includes a sequential dilation system 30 with an initial dilator 32 and one or more additional dilators 34 of increasing diameter, and a tissue retractor assembly 36. As will be appreciated, the initial dilator 32 is preferably advanced to the target site first, and then each of the additional dilators 34 of increasing diameter are advanced in turn over the previous dilator. A k-wire (not shown) may be advanced to the target site and docked in place (for example, by inserting the k-wire into the vertebral disc) prior to, in concurrence with, or after advancing the initial dilator 32 to the target site.

With the sequential dilation system 30 positioned adjacent the target site (and optionally docked in place via a k-wire), the retractor assembly 36 is advanced to the target site over the sequential dilation system 30. According to the embodiment shown, the retractor assembly 36 includes retractor blades 38, 40, 42 and a body 44. With the sequential dilation system 30 removed, the retractor blades 38, 40, and 42 are separated (FIG. 4), providing the lateral access corridor through which instruments may be advanced to prepare the disc space and insert the implant 10. According to one example, the posterior blade 38 may be fixed in position relative to the spine prior to opening the retractor blades. This may be accomplished, for example by attaching a shim 45 to the blade 38 (e.g. via track 46 including dove tail grooves 48 formed on the interior of blade 38) and inserting the distal end of the shim 45 into the disc space. In this manner, the posterior blade 38 will not move posteriorly (towards nerve tissue located in the posterior portion of the psoas muscle 28). Instead, the blades 40 and 42 will move away from the posterior blade 38 to expand the access corridor. Additionally, nerve monitoring (including determining nerve proximity and optionally directionality) is performed as at least one component of the access system, and preferably each component of the access system 22 is advanced through the psoas muscle 28, protecting the delicate nerve tissue running through the psoas, as described in the '949 and '840 patents. Monitoring the proximity of nerves also allows the posterior blade 38 of the retractor assembly 36 to be positioned very posterior (all the way back to the exiting nerve roots), thus exposing a greater portion of the disc space than would otherwise be safely achievable. This in turn permits full removal of the disc and implantation of an implant with a wider footprint implant. Use of a wider footprint meanwhile makes utilization of a hyper-lordotic implant with a large lordotic angle (e.g. between 20-40 degrees) more practical.

With the lateral access corridor formed (as pictured in FIG. 4) the target site may be prepped for insertion of the implant 10. Preparation of the disc space may include performing an annulotomy, removal of disc material, and abrasion of the endplates. Instruments such as annulotomy knives, pituitaries, curettes, disc cutters, endplate scrapers may be used during disc preparation. Additionally, as discussed above, it may be necessary to release the ALL 16 in order to create enough flexibility between the adjacent vertebrae (e.g. V1 and V2) to receive the hyper-lordotic implant 10. Unlike an anterior approach (where the great vessels and other tissue lying anterior to the disc space are retracted during the approach), when the target disc is approached laterally, the great vessels remain adjacent to the ALL along the anterior face of the spine. Thus, while cutting the ALL is generally simple and necessary during an anterior approach surgery, cutting the ALL during a lateral approach surgery has typically been unnecessary and can be difficult because of the need to avoid damaging the great vessels. Accordingly, FIGS. 5-23 set forth various example embodiments of ALL resecting instruments for safely releasing the ALL from a lateral approach.

Figure 5:
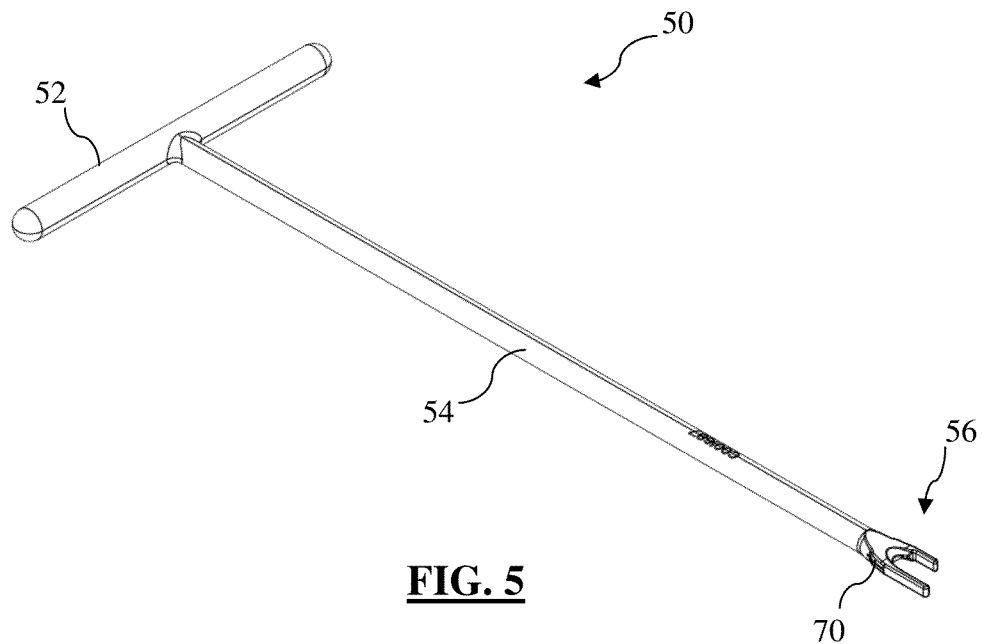
FIG. 5 is a front perspective view of an anterior longitudinal ligament (ALL) resector for safely releasing the ALL through a lateral access corridor, according to one example embodiment.
Figure 6:
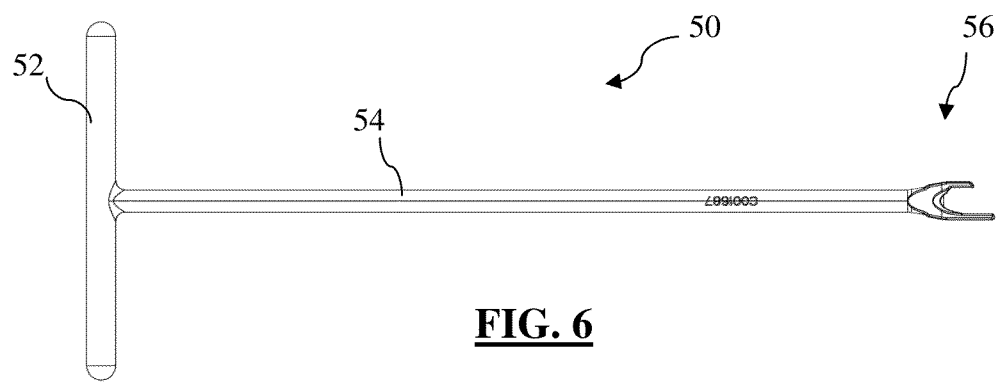
FIG. 6 is a side view of the ALL resector of FIG. 5.
Figure 7:
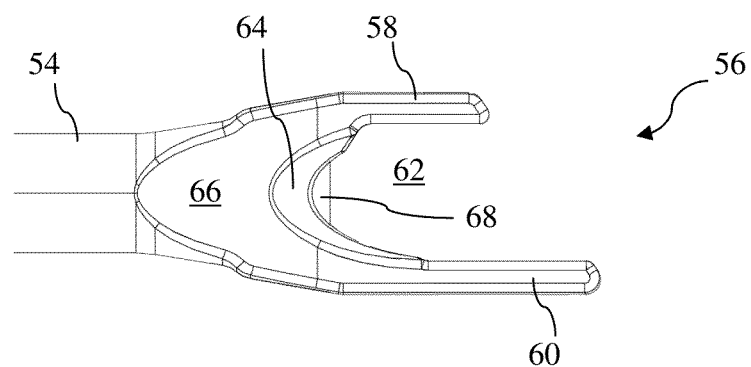
FIG. 7 is an enlarged side view of the distal end of the ALL resector of FIG. 5.

FIGS. 5-7 illustrate an example embodiment of an ALL resector 50. By way of example only, the ALL resector 50 can be used to release (by way of cutting) the ALL anterior to the operative disc space in surgeries requiring a large degree of curvature correction (for example, greater than 15 degrees). The ALL resector 50 includes a handle 52 (for example, a T-handle) located at the proximal end of the elongated shaft 54 and a distal head 56 for resecting the ALL 16. The distal head 56 includes distally extending first and second fingers 58, 60, which form an opening 62 therebetween. First and second tapered surfaces 64, 66 which extend a distance from the elongated shaft 54 along the fingers 58, 60 enable the distal head 56 to insert gently between tissue. As best shown in FIG. 7, the first finger 58 may be shorter in length than the second finger 60. This may serve a variety of purposes, which include giving the user greater viewing capabilities of the cutting area due to a shorter first finger 58 while providing greater protection and insertion guidance with a longer second finger 60. However, the first and second finger 58, 60 may be provided in any number of length configurations without departing from the scope of the present invention. By way of example, it has been contemplated that the first finger 58 may be completely removed. Alternatively the fingers may be curved (as illustrated in the embodiment depicted in FIGS. 8-9) and have a more substantial width than shown in FIGS. 5-7. Curvature of the first and second fingers may allow the distal head 56 to follow closely along the anterior side of the spine and/or along a curved spatula (not shown) positioned adjacent the anterior side of the vertebral body. Though not shown, a user may optionally insert a spatula along the anterior portion of the ALL 16 prior to inserting the ALL retractor 50. The spatula may serve as additional protection between the delicate tissue anterior to the ALL and the cutting blade 68 of the ALL resector 50. With a spatula in place the user may insert the distal head 56 such that it approaches the lateral side of the ALL 16 and is guided along the inside edge of the spatula. By way of example, the spatula may be straight or curved to match the selected fingers of the distal head 56.

A cutting blade 68 is exposed between the first and second fingers 58, 60 in the opening 62. A slot 70 formed along a side of the distal head 56 allows a cutting blade 68 to be inserted and removed from the distal head 56 as needed (such as, for example, if a blade were to become dull or bent). Thus, the cutting blade 68 may be disposable and the remainder of the ALL resector 50 may be reusable. Alternatively, both cutting blade 68 and remainder of the ALL resector 50 may be reusable or both may be disposable. In use, the ALL resector 50 is preferably positioned such that the second finger 60 is aligned along the anterior side of the ALL and the first finger 58 is aligned along the posterior side of the ALL 16, thus, at least partially bounding the ALL 16 on either side which allows the cutting blade 68 to maintain a generally perpendicular alignment relative to the length of the ALL 16. The ALL resector 50 is advanced forward so that the cutting blade 70 cuts through the ALL 16 from one lateral edge to the other. As discussed above, the second finger 60 is preferably aligned along the anterior side of the ALL 16 as the distal head 56 is advanced, thereby shielding the tissue lying anterior to the finger 60 (e.g. great vessels, etc. . . . ) from the cutting blade 68. Furthermore, as the user advances the ALL resector 50, the fingers 58, 60 may also act as a stabilizing guide.

Figure 8:
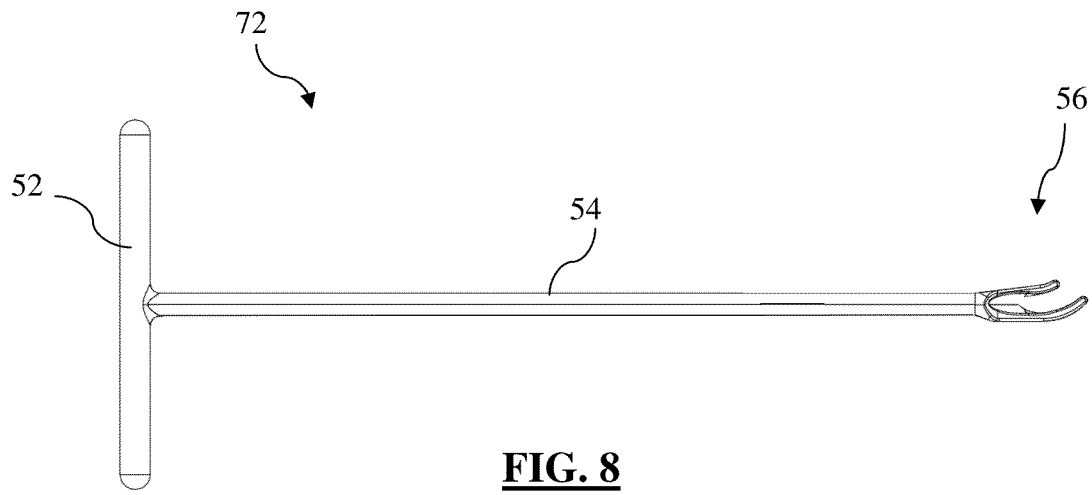
FIG. 8 is a side view of an ALL resector for safely releasing the ALL through a lateral access corridor, according to another example embodiment.
Figure 9:
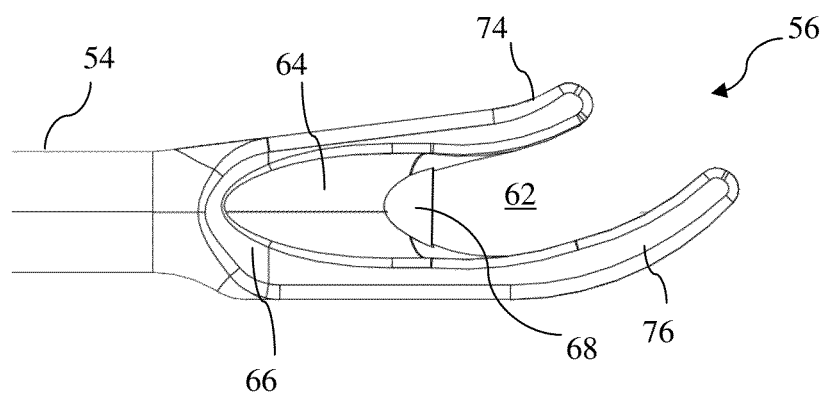
FIG. 9 is an enlarged side view of the distal end of the ALL resector of FIG. 8.
Figure 10:
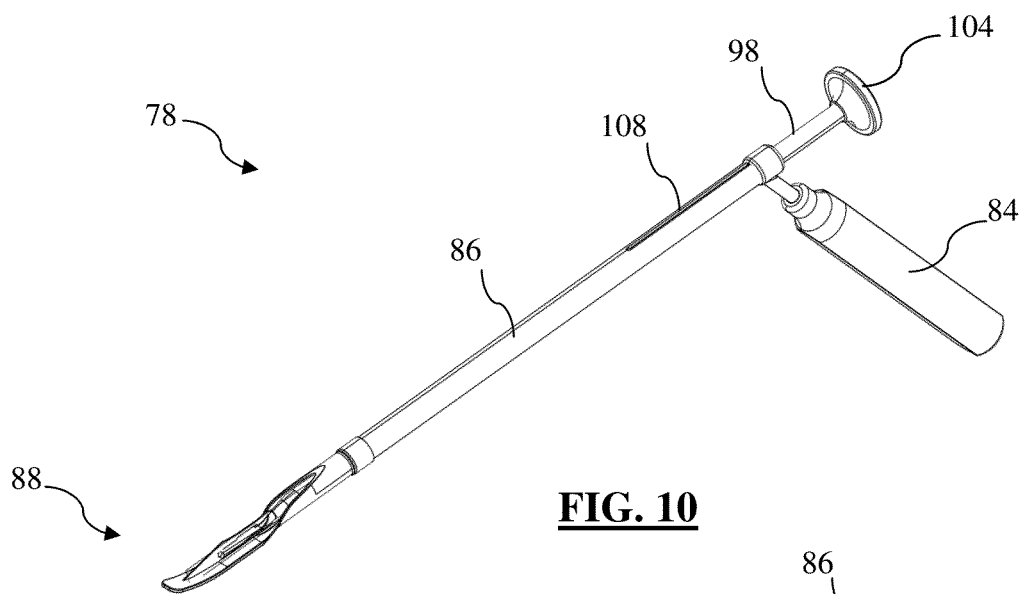
FIG. 10 is a front perspective view of an ALL resector for safely releasing the ALL through a lateral access corridor, according to another example embodiment.
Figure 11:
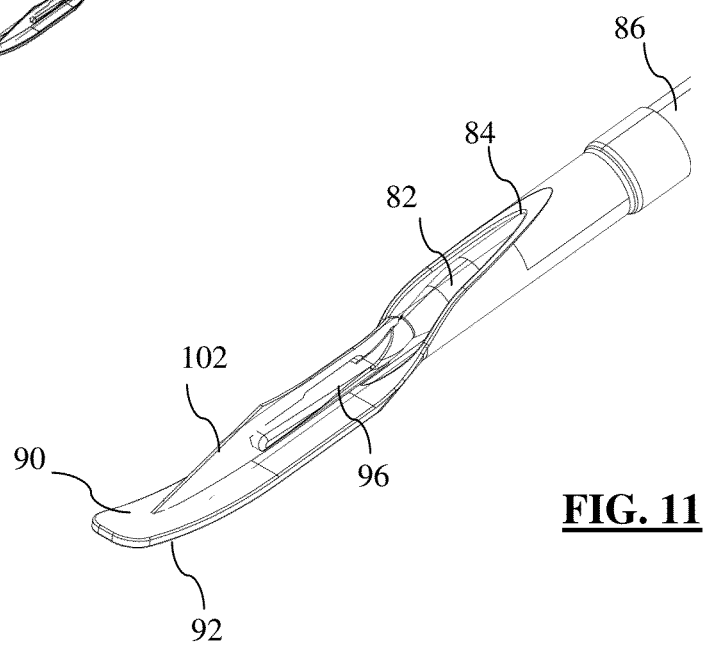
FIG. 11 is an enlarged perspective view of the distal portion of the ALL resector of FIG. 10.
Figure 12:
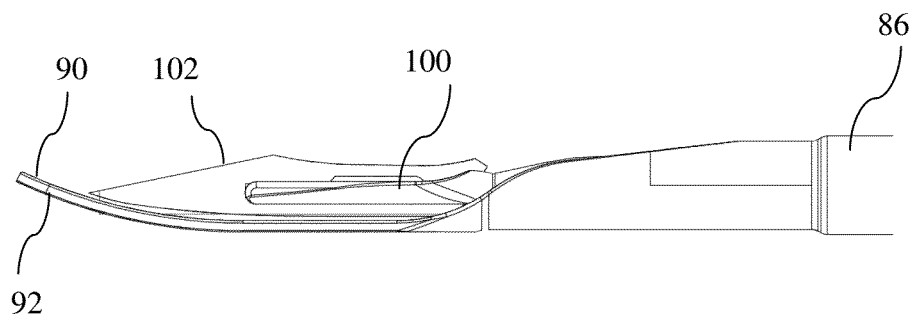
FIG. 12 is an enlarged side view of the distal portion of the ALL resector of FIG. 10.
Figure 13:
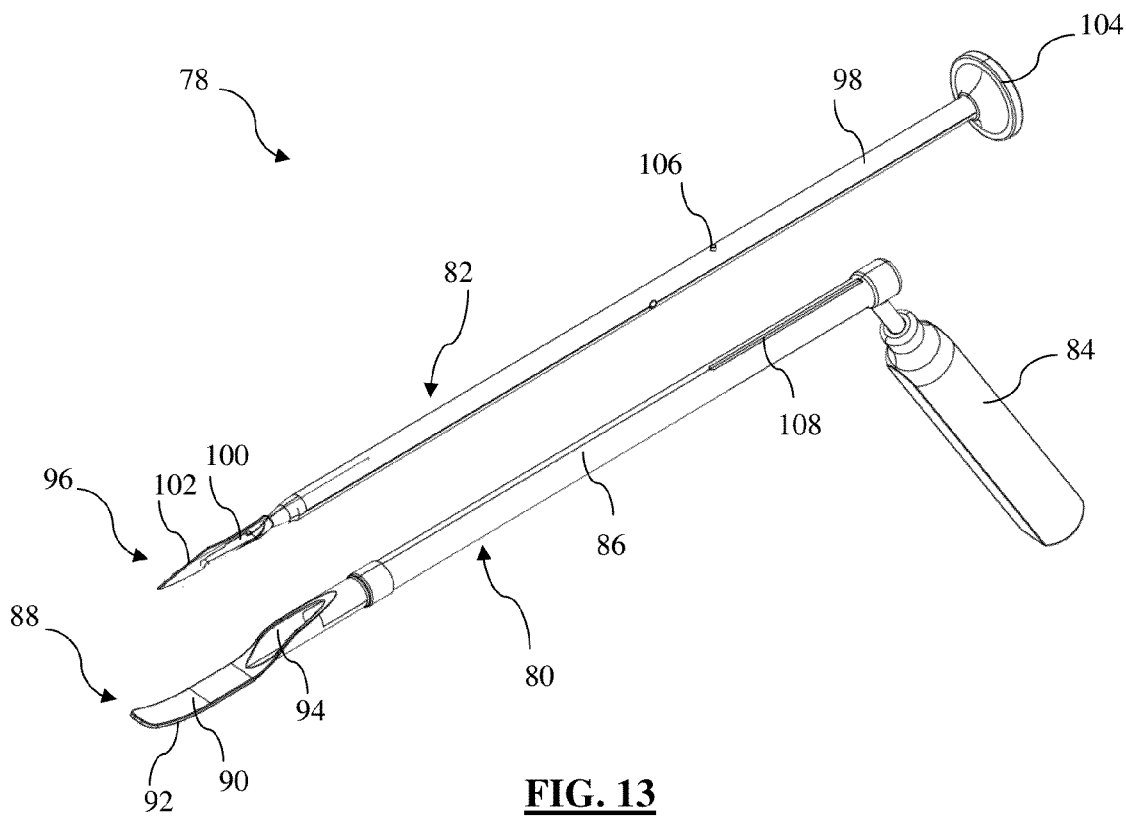
FIG. 13 is an exploded front perspective view of the ALL resector of FIG. 10.

FIGS. 8-9 illustrate an ALL resector 72 according to a second example embodiment. The ALL resector 72 differs from the ALL resector 50 in that its first and second fingers 74, 76 are generally curved. The remainder of the features and functions of the ALL resector 72 are essentially the same as the features and functions of the ALL resector 50 such that they will not be repeated here. The curvature of the first and second fingers 74, 76 allow the distal head 56 to follow closely along the anterior aspect of the spine. By way of example, the curvature of the second finger 76 allows the distal head 56 to more easily slide along a curved spatula (not shown) positioned adjacent to the anterior aspect of the vertebral body. Both the curved spatula and first and second fingers 74, 76 are curved to generally mimic the curvature of the anterior aspect of the spine. This enables a surgeon to more easily maneuver the distal head 56 while cutting across the ALL 16.

Additionally, it has been contemplated that the first and second fingers 74, 76 be sized and shaped to have a greater width than the first and second fingers 58, 60 of ALL resector 50. Added width of the fingers may provide for increased protection and shielding of the cutting area while adding greater stability during insertion.

FIGS. 10-13 illustrate an ALL resector 78 according to a third example embodiment. The ALL resector 78 includes a tissue retractor 80 and a sliding blade 82 which function to both cut the ALL 16 and protect surrounding tissue, blood vessels, and nerves from unwanted damage (similar to the previous embodiments discussed above with reference to ALL resectors 50 and 72). The tissue retractor 80 includes a handle 84, hollow shaft 86, and head 88. The head 88 is curved, preferably such that the inside surface 90 complements the curvature of the anterior aspects of the spinal target site. The head 88 may thus be positioned through the lateral access corridor to the spine and such that the curved interior surface 90 nestles around the curved anterior aspect of the spine. The outside surface 92 will form a barrier, protecting tissue along the anterior spine from inadvertent contact with the sliding blade when the ALL 16 is cut. Furthermore, the tissue retractor 80 can be further manipulated to move tissue and further expose the anterior aspect of the target site. The hollow shaft 86 includes a central lumen 94 with an opening adjacent the head 88 and another opening at the opposing end such that the sliding blade 82 may travel through the shaft 86.

The sliding blade 82 includes a blade 96 that is secured to the distal end of an extender 98 by way of an attachment feature 100. The attachment feature 100 as shown is similar to known attachment features used for attaching a blade at the end of a scalpel. It will be appreciated that any number of mechanisms may be used to attach blade 96 to extender 98. Blade 96 may be disposable and extender 98 may be reusable. Alternatively, both blade 96 and extender 100 may be reusable or both may be disposable. The blade 96 includes a cutting edge 102 that, when advanced beyond the lumen 94 of shaft 86, cuts through tissue or material situated adjacent the cutting edge 102.

The proximal end of the extender 98 includes a grip 104 that a surgeon or other user may use to manipulate the position of the sliding blade 82 relative to the shaft 86 and head 88. At least one stop feature 106 extends from the outer surface of the extender 98 which engages with a track 108 that extends along a portion of the elongated shaft 86. The track 108 limits the longitudinal travel of the sliding blade 82 relative to the shaft 86 so that the sliding blade 82 remains slidably mated to the tissue retractor 80 without becoming unassembled and such that the blade 96 cannot extend beyond the protective head 88. Additionally, the stop feature 106 restricts rotation of the sliding blade 82 relative to the tissue retractor 80.

Figure 14:
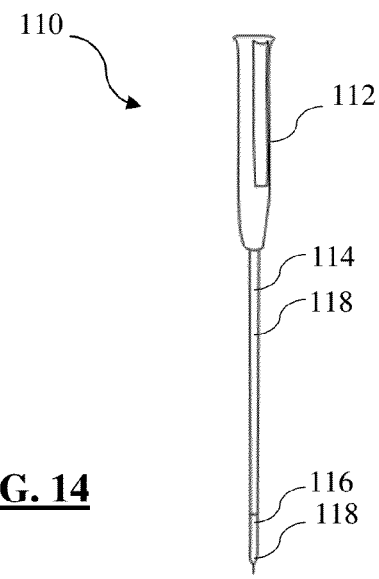
FIG. 14 is a front view of an ALL resector for safely releasing the ALL through a lateral access corridor, according to another example embodiment.
Figure 15:
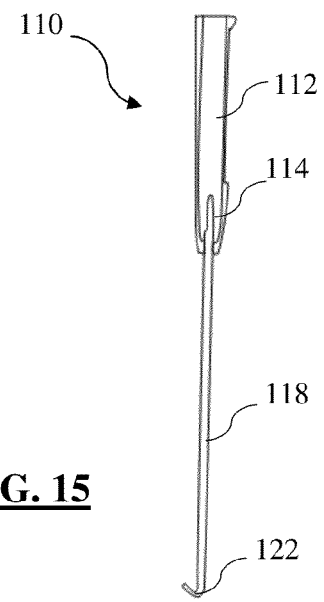
FIG. 15 is a cross-section front view of the ALL resector of FIG. 14.

FIGS. 14-20 illustrate an ALL resector 110 according to a fourth example embodiment. As shown in FIGS. 14-15, the ALL resector 110 is comprised of a handle 112, a conductive shaft 114, a bendable region 116, an anode tip 118, and an electrical connector (not shown).

Preferably, the conductive shaft 114 is coated with an insulative coating 118 about its exterior surface. In some embodiments, the bendable region 116 may be generally hook-shaped 120 such that the anode tip 118 would be oriented in an optimal angle for resecting the ALL 16 from the lateral approach. Alternatively, the bendable region 116 may be generally straight in shape such that customizable bending may be achieved as will be described below.

Figure 16:
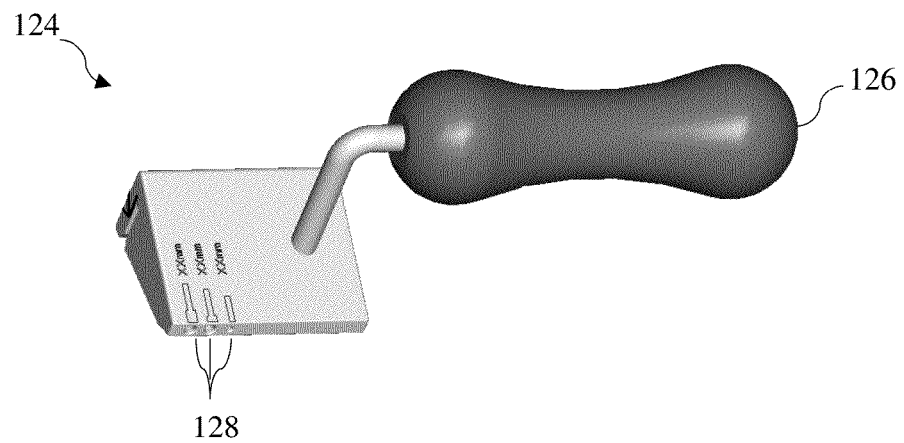
FIG. 16 is a perspective view of a bending block for use with the ALL resector of FIG. 14 according to one embodiment.
Figure 17:
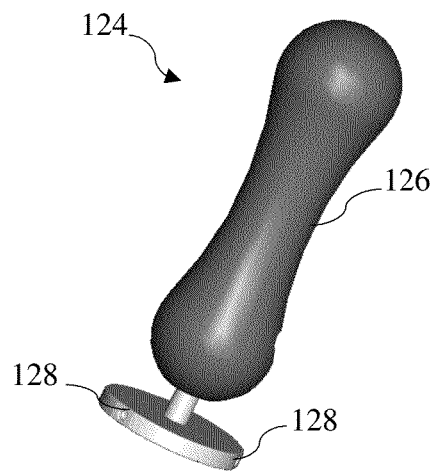
FIG. 17 is a perspective view of a bending block for use with the ALL resector of FIG. 14 according to a second embodiment.
Figure 18:
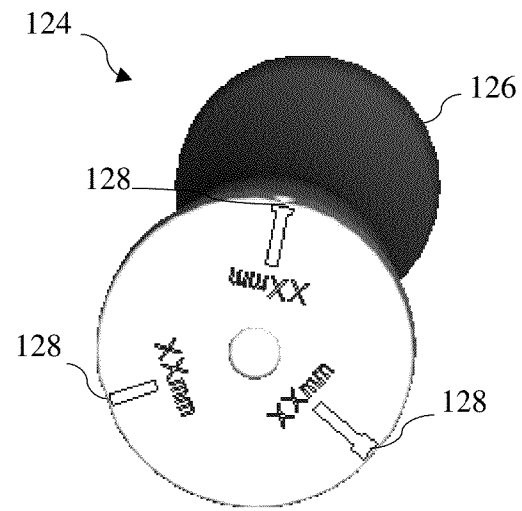
FIG. 18 is a bottom view of the bending block of FIG. 17.

FIG. 16 illustrates a bending block system 122 according to one example embodiment for bending the bendable region 116 of the ALL resector 110. Bending block 122 may be generally square or rectangle-shaped and is comprised of a handle 126 and one or more bending slot 128. The bending slots 128 may be of different lengths such that the bendable region 116 of the ALL resector 110 may be placed in a bending slot 128 and then bent to an appropriate angle for cutting based in part upon considerations of surgeon preference as well as patient anatomy. FIGS. 17-18 illustrate a bending block system 124 according to a second example embodiment. Bending block 124 may be generally circular in shape and comprised of a handle 126 and one or more bending slots 128. Similar to the previous embodiment, the bending slots 128 may be of different lengths such that the bendable region 116 of the ALL resector 110 may be placed in a bending slot 128 and then bent to an appropriate angle for cutting based in part upon surgeon preference as well as patient anatomy restrictions.

Figures 19, 20:
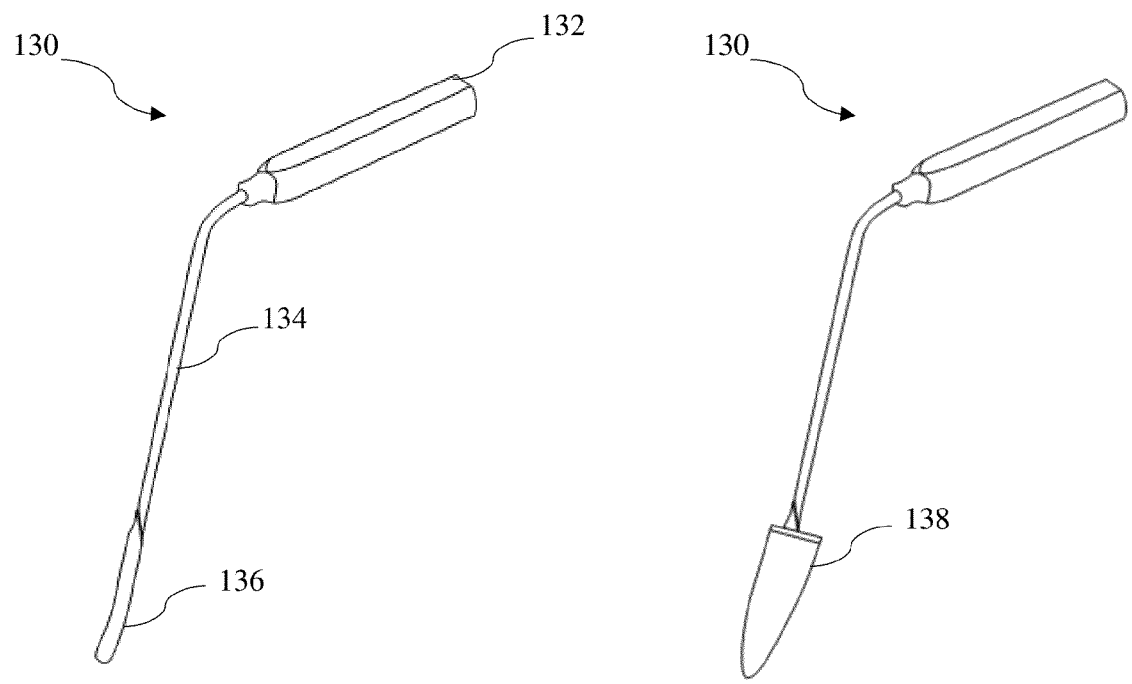
FIG. 19 is a front perspective view of a hand-held retraction tool for use with the ALL resector of FIG. 14.
FIG. 20 is a front perspective view of the hand-held retraction tool of FIG. 19 with an insulative sheath at the tip.

The ALL resector 110 is preferably compatible with a hand-held retraction tool, for example the hand-held retraction tool 130 of FIG. 19. The retraction tool 130 is comprised of a handle 132, a shaft 134, and a paddle 136. The paddle 136 may be bent or straight such that it is able to separate and form a barrier between the great vessels and the ALL resector 110. Preferably, the retraction tool 130 is non-conductive. This may be accomplished by constructing the retraction tool 130 of non-conductive material or by coating the surfaces of the retraction tool with an insulating material. According to one example, the paddle 136 is rigid enough to achieve retract the great vessels without yielding under the weight of the vessels. According to another example, the paddle 136 may be flexible such that it can be inserted under the great vessels and flex up as the ALL resector 110 is advanced underneath the paddle 136 to cut the ALL. As shown in FIG. 20, a protective sheath 138 may surround the paddle 136 of the retraction tool 130 for added protection when the paddle 136 contacts the great vessels.

To use the ALL resector 110, the surgeon may preferably first insert the retraction tool 130 between the ALL 16 and the great vessels, aligning the paddle 136 in a manner that protects the vessels without over-retracting them. The surgeon determines the ideal angle to approach the ALL 16 and whether to use a hooked, straight, or custom-bent tip. Once the ALL resector 110 is prepared with the preferred tip 118, the electrical connector can be connected to an electrosurgical unit that delivers electrical current to the anode tip 118 in an amount that will cauterize (thus cut) the tissue of the ALL. The non-conductive paddle 136 of the retraction tool 130 protects the great vessels from the cauterizing effect of the electrical current.

Figure 21:
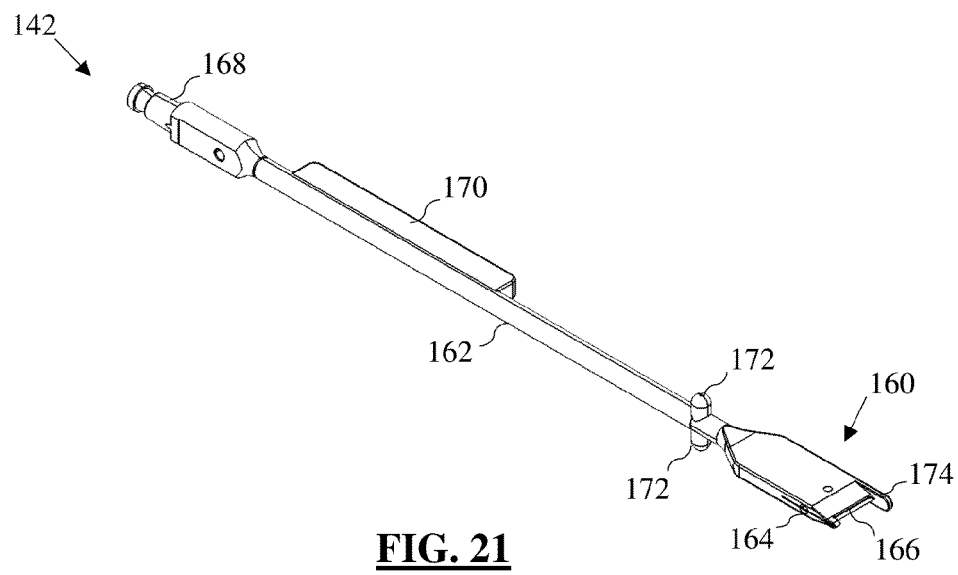
FIG. 21 is a perspective view of an ALL resector for safely releasing the ALL through a lateral access corridor according to another example embodiment.
Figure 22:
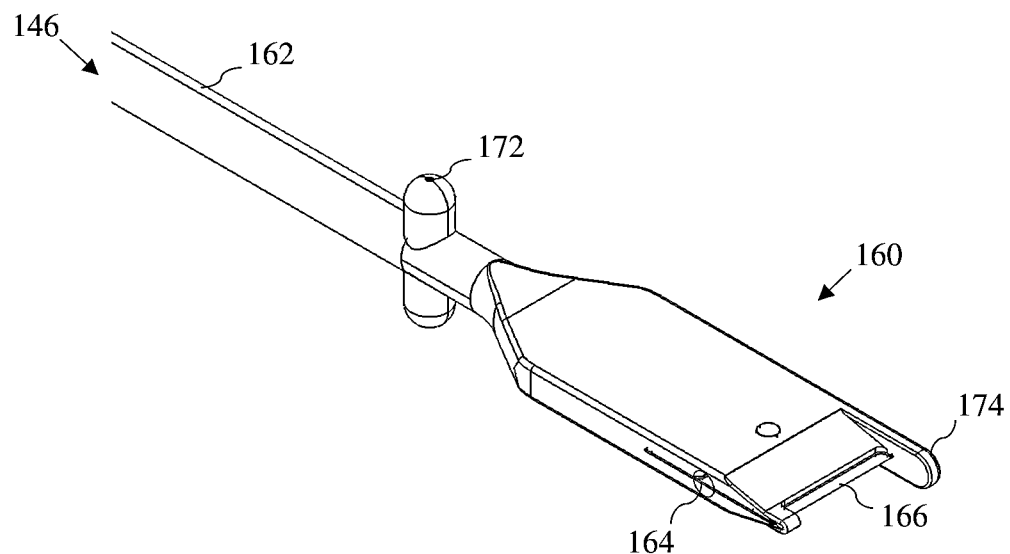
FIG. 22 is an enlarged perspective view of the distal end of the ALL resector of FIG. 21.
Figure 23:
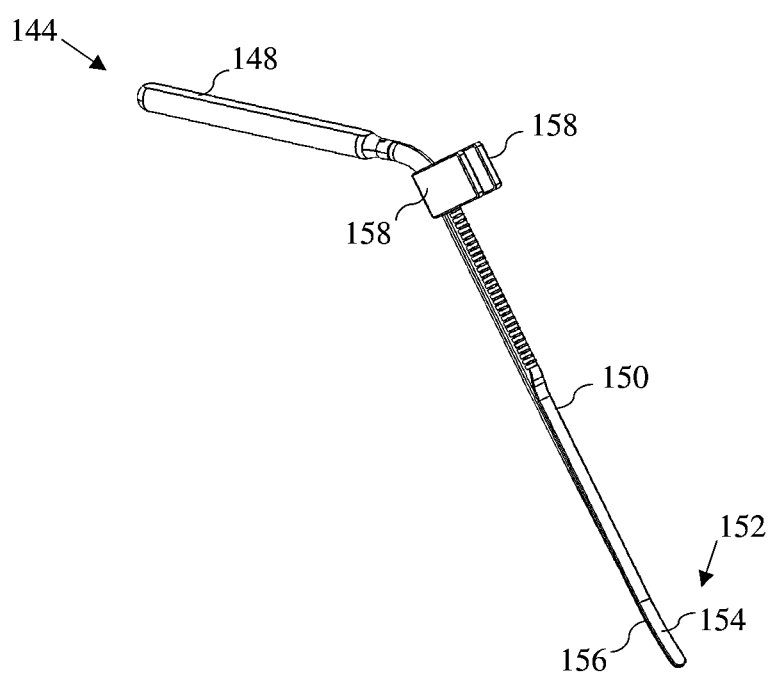
FIG. 23 is a perspective view of a retraction tool for use with the ALL resector of FIG. 21.

FIGS. 21-23 illustrate yet ALL resector 142 according to a fifth example embodiment.

The ALL resector 142 includes a tissue retractor component 144 and a cutter component 146 which work in concert to cut the ALL and protect surrounding tissue, blood vessels, and nerves from unwanted damage (similar to the other ALL resector embodiments discussed above). The tissue retractor 144 protects against anterior migration of the cutter 146 towards the great vessels and includes a handle 148, an elongate shaft 150, and a head 152. The head 152 is curved, preferably in such a way that the inside surface 154 compliments the curvature of the anterior aspects of the spinal target site. The head 152 may thus be positioned through the lateral access corridor to the spine such that the curved interior surface 154 nestles around the curved anterior aspect of the spine. The outside surface 156 will form a barrier, protecting tissue along the anterior spine from inadvertent contact with the cutting edge 166 of the cutter 146 when the ALL 16 is cut. Furthermore, the tissue retractor 144 can be further manipulated to move tissue and further expose the anterior aspect of the target site. The elongate shaft 150 includes two guide posts 158 that are sized and dimensioned to function as a track to allow the cutter 146 to travel between the guide posts 158 and along the length of the elongate shaft 150 as will be described below.

The cutter 146 includes a blade 160 that is secured to the distal end of an extender 162 by way of an attachment feature 164. The attachment feature 164 as shown is similar to known attachment features used for attaching a cutting blade at the end of a scalpel. In the embodiment shown, the blade 160 includes only a single cutting edge 166, however it is contemplated that more than one cutting edge 166 may be utilized. It will be appreciated that any number of mechanisms may be used to attach blade 160 to extender 162. Blade 160 may be disposable and extender 162 may be reusable. Alternatively, both blade 160 and extender 162 may be reusable or both may be disposable. The blade 160 includes a cutting edge 166 that, when advanced along the elongate shaft 150 of the retractor component 144, cuts through tissue or material situated adjacent the cutting edge 166.

The proximal end of the extender 162 includes a connector 168 to which a handle may be connected that a surgeon may use to manipulate the position of the cutter 146 relative to the shaft 150 and head 152. At least one anti-rotation bar 170 extends from the outer surface of the extender 162 which can be slidably inserted between guide posts 158 and travel along a portion of the elongated shaft 150. When the cutter 146 is positioned with the anti-rotation bar 170 between the guide posts 158, the guide posts 158 keeps the cutter 146 slidably mated to the tissue retractor 144 and restricts rotation of the cutter 146 relative to the tissue retractor 144. Further, the cutter 146 is restricted from movement in the cephalad/caudal direction by the vertebral bodies V1 and V2. Additionally, the extender 162 includes a pair of distal wings 172 protruding generally perpendicularly from the outer surface of the extender 162. Distal wings 172 are sized and dimensioned to contact the proximal surfaces of V1 and V2 when the blade 160 is fully advanced across the ALL in order to act as a depth stop and restrict excessive advancement of the cutting blade 160. The cutting blade 160 may also be provided with an elongated finger 174 as shown in FIG. 22, that may be used for further protection of nearby tissue (for example, the posterior longitudinal ligament or the great vessels) and as stabilizer during use.

While the ALL resectors 50, 72, 78, 110,142 are susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the scope and spirit of the invention as defined herein. Furthermore, the ALL resectors 50, 72, 78, 110, 142 may be incorporated into a surgical kit or used with any number of various tooling and/or implants. The following are examples of tooling and implants that may be used in conjunction with the ALL resectors discussed herein, as well as any variation of an ALL resector not disclosed herein.

As discussed above, a patient may undergo a lateral procedure and have an intervertebral disc space prepared for the permanent implantation of, for example, a hyperlordotic implant. The intervertebral space may be prepared via any number of well-known surgical preparation tools, including but not limited to, kerrisons, rongeurs, pituitaries, and rasps. Preparation of the disc space may also include the removal of any implants already occupying the disc space. By way of example only, during a revision surgery, it may be necessary to remove a spinal fusion implant or TDR device previously implanted.

Once the disc space is prepared, the surgeon may designate the appropriate implant size. This may be accomplished through the use of a trial sizer (not shown). The trial sizer may include grooves along at least a portion of the upper and/or lower surfaces to help insert the sizer along the desired path through the intervertebral space. The sizer may also be connected to a guide clip attachment that can be guided along the retractor blade 38 of the retractor assembly (as will be described below in connection with the implant insertion). When the appropriate size is determined, an insertion instrument, for example, insertion instrument 310 may then be secured to an implant such that the implant is advanceable into the prepared intervertebral disc space.

Figure 27:
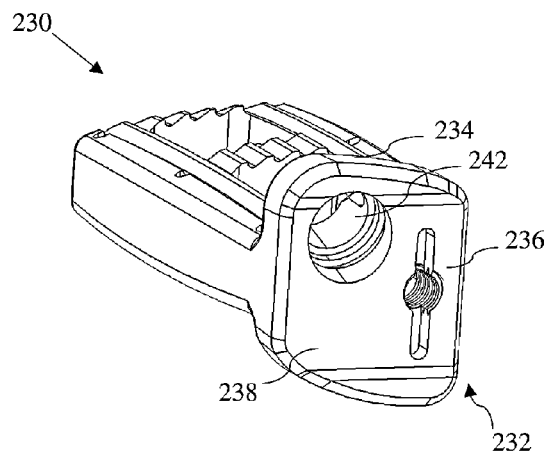
FIG. 27 is a posterior side perspective view of a hyper-lordotic implant according to a second example embodiment.

Turning now to FIGS. 24-48, various embodiments of a hyper-lordotic implant for insertion through a lateral approach are described. FIGS. 24-26, for example, illustrate an implant 200 according to a first embodiment. Implant 200 may preferably be comprised of any suitable non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK. Other materials such as for example, metal, ceramics, and bone may also be utilized for the implant 200. Implant 200 has a top surface 202 and bottom surface 204 for contacting V1 and V2, anterior sidewall 206, posterior sidewall 208, and front or leading side 210, and rear or trailing side 212. As discussed, the anterior sidewall 206 has a height greater than the posterior sidewall 208 such that the top surface 202 and bottom surface 204 converge towards each other in the posterior direction. As shown in FIG. 27, the angle of convergence is represented by a. By way of example, the top and bottom surfaces may converge at an angle between 20 and 40 degrees. It is contemplated that variations of the implant 200 may be simultaneously provided such that the user may select from different available ranges. For example, variations may be provided with 20 degree, 30 degree, and 40 degree angles. The top and bottom surfaces may be planar or provided as convex to better match the natural contours of the vertebral end plates. The top surface 202 and the bottom surface 204 may be interchangeable (i.e. the implant may be flipped) such that the same implant may be implanted from either the left or right side of the patient.

The implant 200 may be provided with any number of additional features for promoting fusion, such as fusion apertures 214 extending between the top and bottom surfaces 202, 204 which allow a boney bridge to form through the implant 200. Various osteoinductive materials may be deposited within the apertures 214 and/or adjacent to the implant 200 to further facilitate fusion. Such osteoinductive materials may be introduced before, during, or after the insertion of the exemplary spinal fusion implant 200, and may include (but are not necessarily limited to) autologous bone harvested from the patient receiving the spinal fusion implant, bone allograft, bone xenograft, any number of non-bone implants (e.g. ceramic, metallic, polymer), bone morphogenic protein, and bio-resorbable compositions, including but not limited to any of a variety of poly (D,L-lactide-co-glycolide) based polymers. Visualization apertures 216 situated along the sidewalls, may aid in visualization at the time of implantation and at subsequent clinical evaluations. More specifically, based on the generally radiolucent nature of the preferred embodiment of implant 200, the visualization apertures 216 provide the ability to visualize the interior of the implant 200 during X-ray and/or other imaging techniques. Further, the visualization apertures 216 will provide an avenue for cellular migration to the exterior of the implant 200. Thus the implant 200 will serve as additional scaffolding for bone fusion on the exterior of the implant 200.

The spinal fusion implant 200 may be provided in any number of sizes by varying one or more of the implant height, width, and length. The length of the implant 200 is such that it may span from one lateral aspect of the disc space to the other, engaging the apophyseal ring on each side. By way of example, the implant 200 may be provided with a length between 40 mm and 60 mm. The size ranges described are generally appropriate for implantation into the lordotic lumbar portion of the spine. The dimensions of the implant 200 may be altered according to proportions of the particular patient. Further, variation of the implant dimensions may be implemented to produce implants generally appropriate for implantation into any portion of the spine. By way of example only, the posterior sidewall 208 may be dimensioned at a height greater than that of anterior sidewall 206 such that top surface 202 and bottom surface 204 converge toward one another at the anterior sidewall 206 (e.g. to create a hyper-kyphotic implant) in order to promote the proper kyphotic angle in the thoracic spine.

As shown in FIGS. 24-25, the implant 200 may include anti-migration features designed to increase the friction between the spinal fusion implant 200 and the adjacent contact surfaces of the vertebral bodies, and thereby minimize movement or slippage of the implant 200 after implantation. Such anti-migration features may include ridges 220 provided along the top surface 202 and/or bottom surface 204. Additional anti-migration features may also include spike elements 222 disposed along the top 202 and bottom surfaces 204. The spike elements 222 may be manufactured from any of a variety of suitable materials, including but not limited to, a metal, ceramic, and/or polymer material, preferably having radiopaque characteristics. The spike elements 222 may each comprise a unitary element extending through the top surface 202 and bottom surface 204. Alternatively, each spike element 222 may comprise a shorter element which only extends to a single surface. In any event, when the spike elements 222 are provided having radiodense characteristics, and the implant 200 is manufactured from a radiolucent material (such as, by way of example only, PEEK or PEKK), the spike elements 222 will be readily observable under X-ray or fluoroscopy such that a surgeon may track the progress of the implant 200 during implantation and/or the placement of the implant 200 after implantation.

Tapered surfaces 224 may be provide along the leading end 210 to help facilitate insertion of the implant 200. Additional instrumentation may also be used to help deploy the implant 200 into the disc space. By way of example, the implant installation device shown and described in detail in the commonly owned and copending U.S. patent application Ser. No. 12/378,685, entitled "Implant Installation Assembly and Related Methods," filed on Feb. 17, 2009, the entire contents of which is incorporated by reference herein, may be used to help distract the disc space and deposit the implant therein.

The spinal fusion implant 200 may be provided with any number of suitable features for engaging the insertion instrument 310 (illustrated in FIG. 49). As best viewed in FIG. 24, one such engagement mechanism involves a threaded receiving aperture 226 in the posterior sidewall 208 of the implant 200. The threaded receiving aperture 226 is dimensioned to threadably receive a threaded connector 182 on the insertion instrument 310. In addition to the receiving aperture 226, the implant 200 is preferably equipped with a pair of grooved purchase regions 228 extending either generally vertically or generally horizontally from either side of the receiving aperture 226. The grooved purchase regions 228 are dimensioned to receive corresponding distal head plates 326 on the insertion instrument 310. Together, these engagement mechanisms provide an enhanced engagement between the implant 200 and insertion instrument 310 and prevent unwanted rotation of the implant 200 during insertion as will be described in greater detail below. Having been deposited in the disc space, the implant 200 facilitates spinal fusion over time by maintaining the restored curvature as natural bone growth occurs through and/or past the implant 200, resulting in the formation of a boney bridge extending between the adjacent vertebral bodies V1 and V2.

Figure 28:
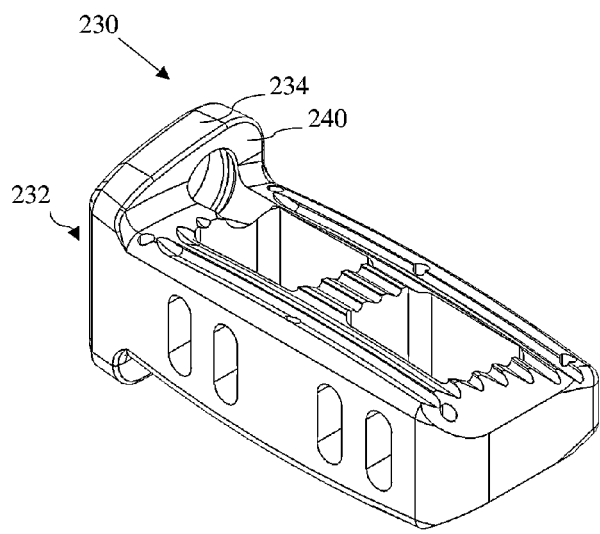
FIG. 28 is an anterior side perspective view of the hyper-lordotic implant of FIG. 27.
Figure 29:
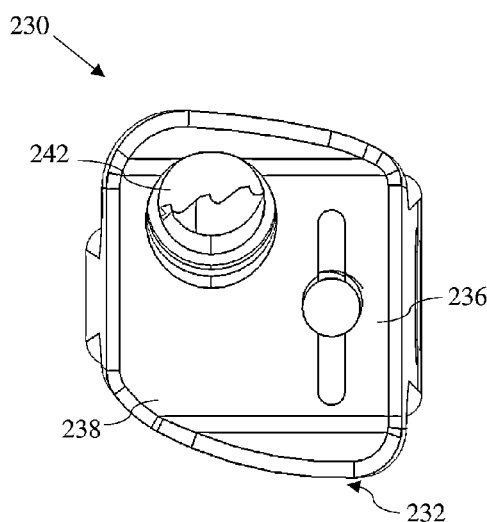
FIG. 29 is a lateral side view of the hyper-lordotic implant of FIG. 27.

FIGS. 27-29 illustrate an implant 230 according to a second example embodiment of a hyper-lordotic implant. The implant 230 shares many similar features with the implant 200 such that repeat discussion in not necessary. The implant 230 differs from the implant 200 in that a trailing side 212 is configured for fixed engagement to one of the adjacent vertebral bodies (i.e. V1 or V2) to supplement the anti-migration features and ensure the hyper-lordotic implant is not projected out of the disc space. Specifically, the implant 230 includes a tab 232 extending vertically above the top surface 202 and below the bottom surface 204.

In the example shown, the tab 232 is arcuate at the corners and generally trapezoidal, however, it should be appreciated that the tab 232 may take any number of suitable shapes, such as, by way of example only, square, rectangular, triangular, partially circular, or partially ovular, among others, the tab may be of different lengths. It should also be appreciated that tab 232 surfaces may be one or more of generally concave, generally convex, or generally planar. The tab 232 is comprised of a perimeter surface 234, an anterior side 236, a posterior side 238, and a tab side 240. Anterior side 236 and posterior side 238 may be interchangeable (i.e. the implant may be flipped horizontally or vertically) such that the same implant may be implanted from either the right side or the left side of the patient. Anterior side 236 and posterior side 238 are preferably, though not necessarily, configured coplanar with anterior sidewall 206 and posterior sidewall 208, respectively (i.e. the width of tab 232 is preferably equal to the width of the implant proximal end, however, the width of the tab may be greater than, or less than, the width of the implant at proximal end). Tab side 240 of tab 232 is configured to engage the exterior surface of an adjacent vertebrae.

Figure 42:
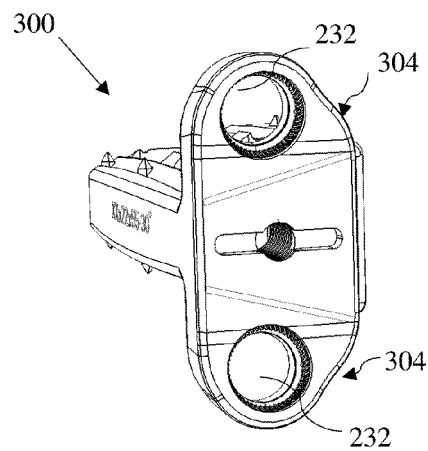
FIG. 42 is a posterior side perspective view of a hyper-lordotic implant according to a sixth example embodiment.
Figure 43:
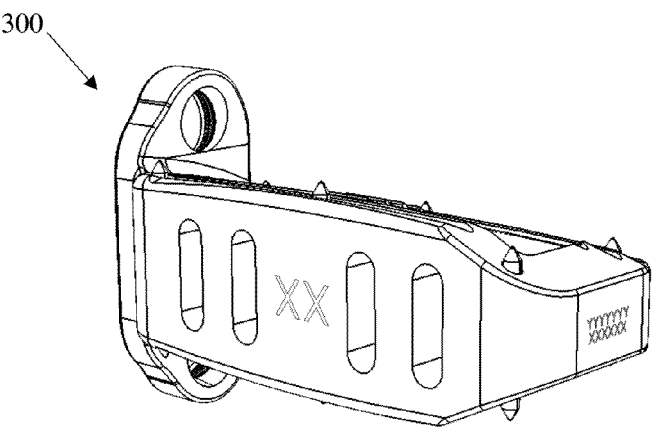
FIG. 43 is an anterior side perspective view of the hyper-lordotic implant of FIG. 42.
Figure 44:
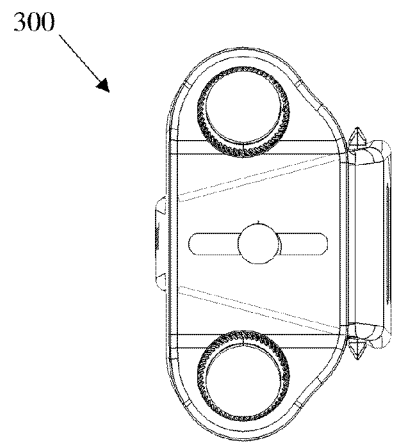
FIG. 44 is a lateral side view of the hyper-lordotic implant of FIG. 42.
Figure 45:
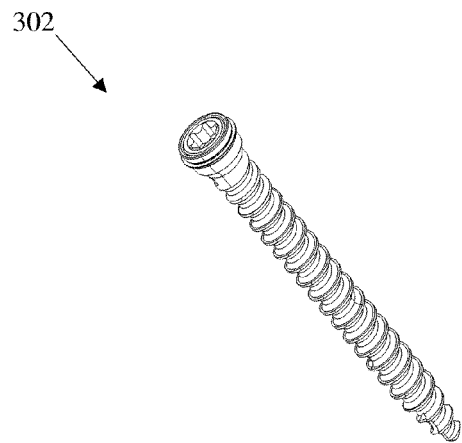
FIG. 45 is a perspective view of an example fixation anchor for securing the position of the hyper-lordotic implant of FIG. 42.
Figure 46:
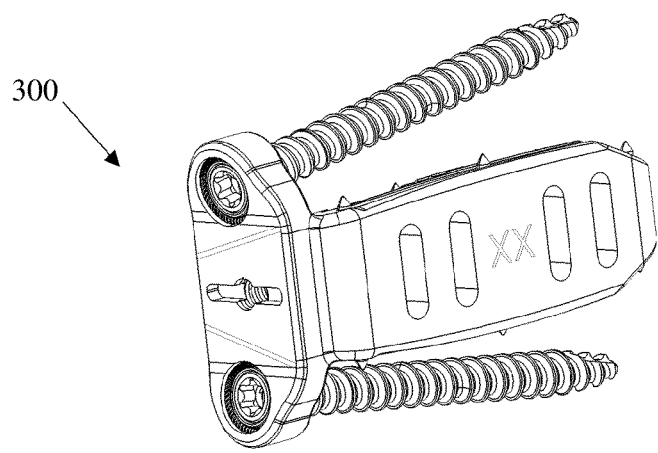
FIG. 46 is an anterior side view of the hyper-lordotic implant of FIG. 42 with the fixation anchors of FIG. 45 positioned.
Figure 47:
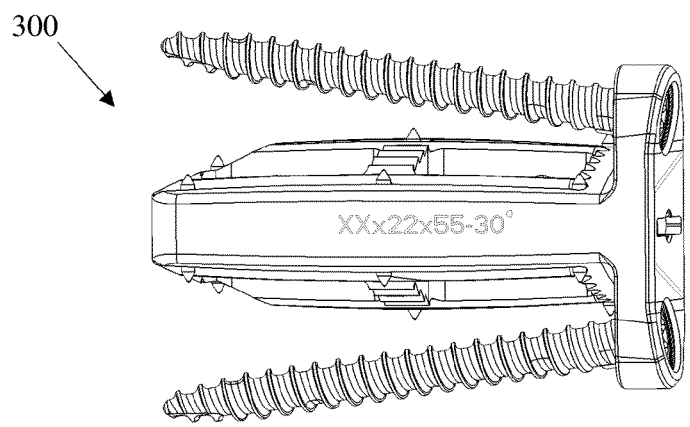
FIG. 47 is posterior side view of the implant and anchors of FIG. 46.
Figure 48:
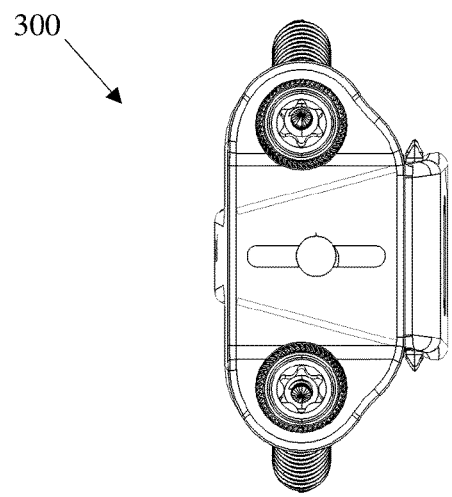
FIG. 48 is a lateral side view of the implant and anchors of FIG. 46.

The tab 232 is provided with a fixation aperture 242 for enabling the engagement of a fixation anchor 302 within the vertebral bone to secure the placement of the implant 230. The fixation aperture 242 may have any number of shapes and/or features for enabling an anchor (for example the fixation anchor 302 of FIG. 45) to engage and secure the positioning of an implant 230. The anchor engages within the vertebral bone through the fixation aperture 242 to secure the placement of the implant 230. In use, when the implant 230 is positioned within the disc space, the tab 232 engages the exterior of the upper and lower vertebra and the anchor 302 may be driven into the side of either the upper or lower vertebra, depending on the orientation of the implant 230. One will appreciate that various locking mechanisms may be utilized and positioned over or within the fixation aperture 234 to prevent the anchor 302 from unwanted disengagement with the implant 230. For example, a suitable locking mechanism may be in the form of a canted coil disposed within the fixation aperture 234 (as illustrated in FIG. 42), or may be engaged to the trailing end 212 and cover all or a portion of the fixation aperture 242 after the anchor 302 is positioned.

Figure 30:
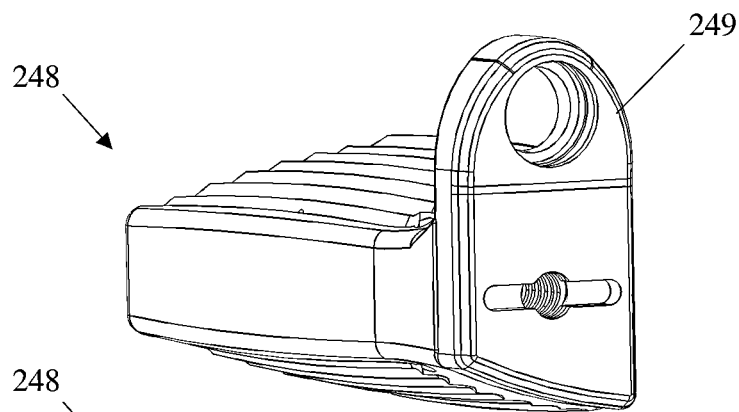
FIG. 30 is a posterior side perspective view of a hyper-lordotic implant according to a third example embodiment.
Figure 31:
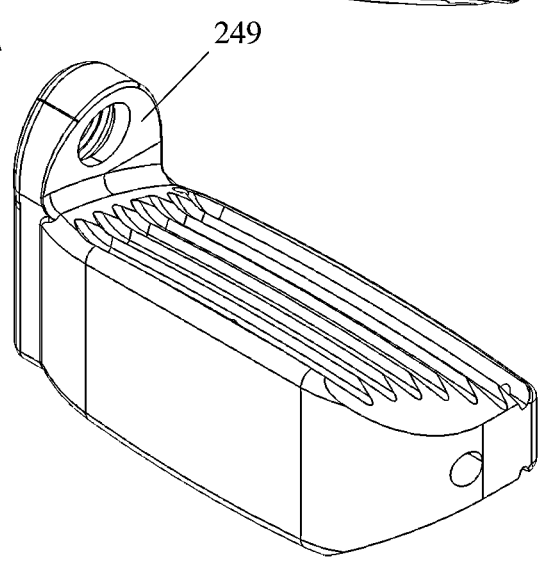
FIG. 31 is an anterior side perspective view of the hyper-lordotic implant of FIG. 30.
Figure 32:
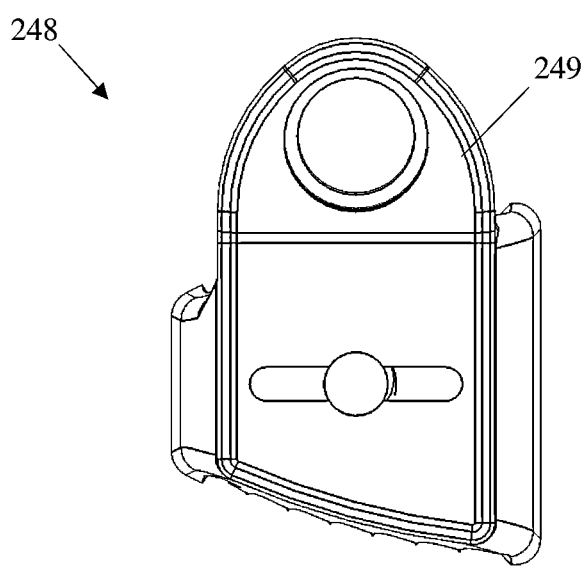
FIG. 32 is a lateral view of the hyper-lordotic implant of FIG. 30.

FIGS. 30-32 illustrate an implant 248 according to a third example embodiment of a hyper-lordotic implant. The implant 248 shares many similar features with the implants 200 and 230 such that repeat discussion of them all is not necessary. The implant 248 differs from the implant 230 in that the tab 249 extends higher (or lower depending on the insertion orientation) from the surface of the implant and solely in one direction such that it only engages the exterior of the upper (or lower) vertebra and the tab 249 has a partially ovular shape where it extends from the implant. Any number of features to prevent the backing out of an anchor may be utilized with this embodiment.

Figure 33:
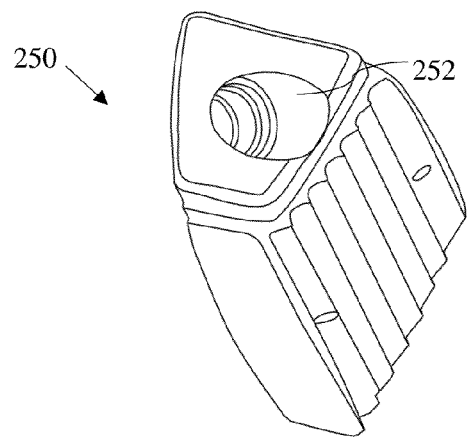
FIG. 33 is a posterior side perspective view of a hyper-lordotic implant according to a fourth example embodiment.
Figure 34:
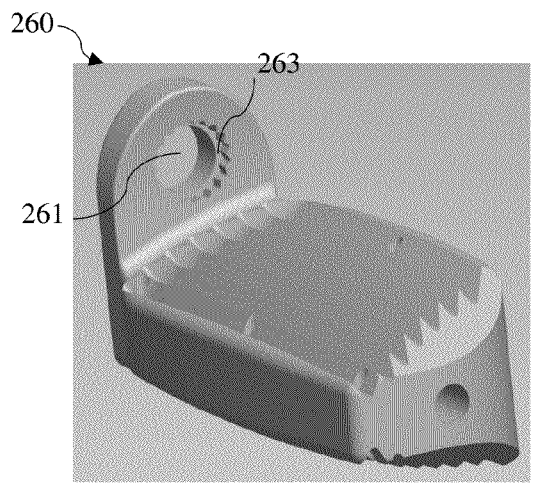
FIG. 34 is a posterior side perspective view of a hyper-lordotic implant according to a fifth example embodiment.
Figure 35:
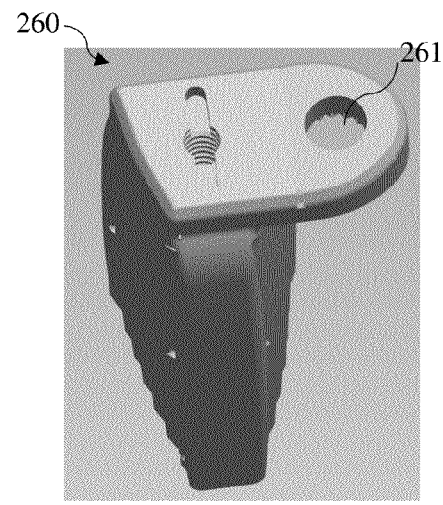
FIG. 35 is another perspective view of the hyper-lordotic implant of FIG. 34.

FIG. 33 illustrates a implant 250 according to a fourth example embodiment a hyper-lordotic implant. The implant 248 shares many similar features with the implants 200, 230, and 248 such that repeat discussion of them all is not necessary. The implant 250 differs from the previous embodiments in that it is configured for fixation to one of the adjacent vertebrae but does not utilize a tab or tabs to do so. Instead, the implant 250 has one or more fixation apertures 252 that travel through the body of the implant 250. The fixation apertures 252 are formed at an angle from a side of the implant such that the anchors will travel through the fixation apertures 252 into the vertebral bodies through the vertebral endplate. Any number of features to prevent the backing out of an anchor may be utilized with this embodiment.

FIGS. 34-41 illustrate a an implant 260 according to a fifth example embodiment of a hyper-lordotic implant. The features and functions are essentially the same as the features and functions described=with reference to the implants 230, 248, and 250 such that they will not be repeated here. However, spinal fusion implant differs from the implants described above in that fixation apertures 261 are configured for engagement with anchors 262 that are anchored into the vertebral bodies before the implant 260 is implanted. FIGS. 36-37 illustrate an example of an anchor 262 specially for use with the implant 260. The anchor 260 is designed to be implanted prior to the implant 260. The anchor 262 includes a head 266 at its proximal end, an intermediate region 268, and an elongated shaft 270 extending distally from the intermediate region 268. The head 266 has a generally cylindrical shape and extends generally perpendicularly in proximal direction from the top of the intermediate region 268. The head 266 includes an exterior threadform 272 configured to engage the locking element 274. In use, the anchor 262 is placed first, and the fixation aperture 261 is fitted over the head 266. The head 266 further includes a recess 276 for receiving a portion of an instrument for insertion (for example, a driver). The recess 276 may have any shape that corresponds to the shape of the distal tip of the driver.

The intermediate region 268 includes a plurality of vertically-oriented chocks 264 distributed in a radial gear-shaped pattern about the anchor 262. The chocks 264 are configured to engage with the contoured periphery 263 of a fixation aperture 252 to provide a solid connection between the anchor 262 and implant 260. The intermediate region 268 further has a sloped distal-facing surface 278 configured to contact the relevant vertebral bodies. The sloped distal-facing surface 278 may have any cross-sectional shape desired by the user, including but not limited to concave, convex, and generally planar.

The elongated shaft 270 extends distally from the intermediate region 268. The shaft 270 includes a threadform 280 configured to provide purchase into the bone. By way of example only, the threadform 280 is provided as a single-lead threadform, however, multiple threads may be used without departing from the scope of the present invention. The shaft 270 further includes a notch 282 to provide the anchor 262 with a self-tapping feature. Further, the anchor 262 may be provided with a lumen 284 extending therethrough such that the anchor 262 is cannulated. The anchor 262 has a major diameter defined by the outer diameter of the threadform 272.

FIGS. 38-39 illustrate an example of a locking element 274 for use with the anchor 262. The locking element 274 includes a central aperture 286 sized and configured to receive the head 266 of the anchor 262 therein. To facilitate this arrangement, the central aperture 286 is provided with a threadform 288 that complements the thread 272 of the head 266. The upper exterior portion 290 is configured to engage the distal end of an insertion device (for example, an inserter). As best seen in FIG. 38, the upper exterior portion 290 has a generally sunburst-shaped cross-section, with a plurality of radial protrusions 292 separated by a plurality of recesses 294.

Figures 40, 41:
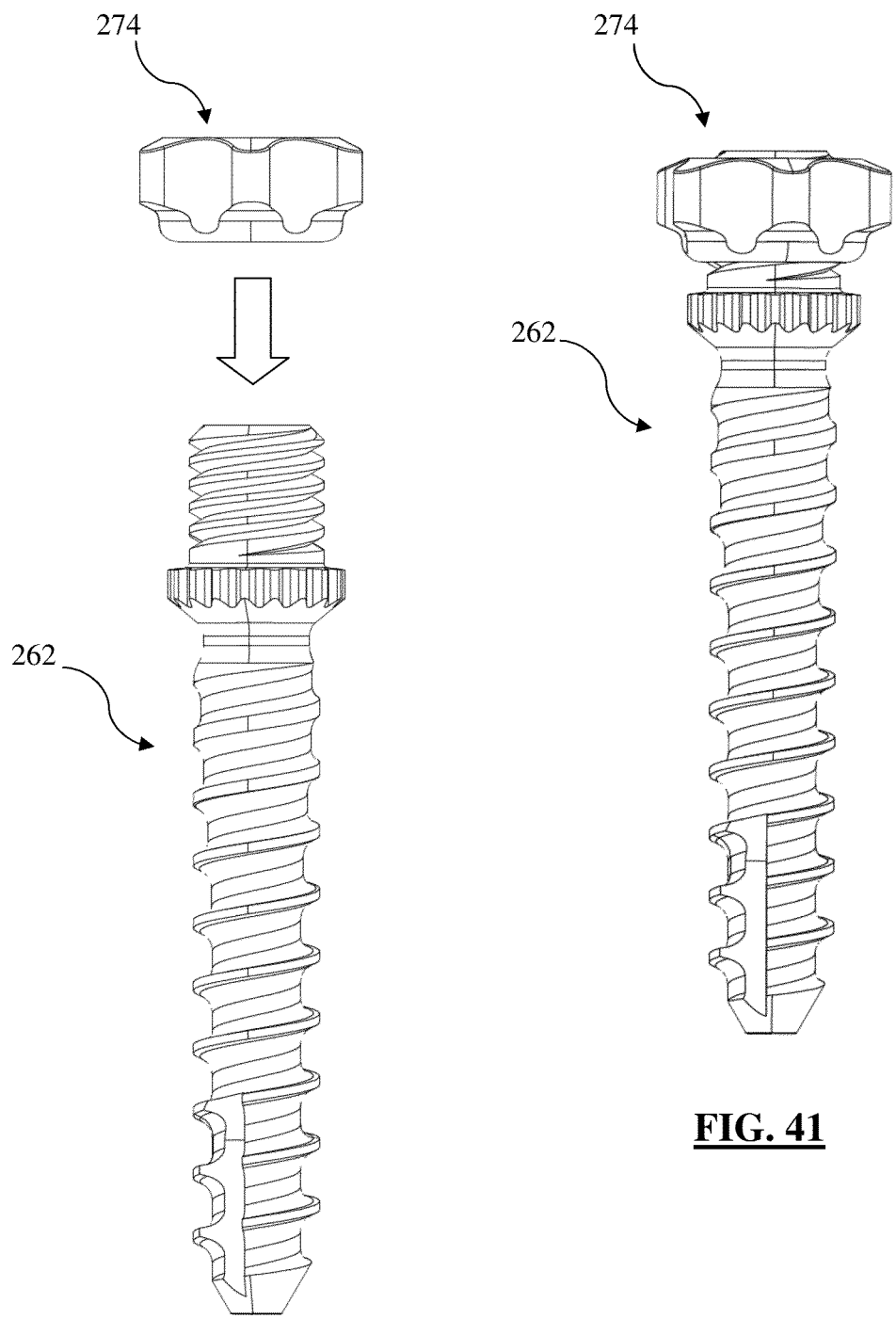
FIGS. 40-41 illustrate the locking element of FIG. 38 being engaged to the anchor of FIGS. 36 and 37.

FIGS. 40-41 illustrate the engagement of the locking element 274 with the anchor 262. To achieve this, the locking element 274 is advanced onto the head 266 of the anchor 262 which extends out of the fixation aperture 242 of the implant 260. The thread 288 of the locking element 274 cooperates with the head 266 to create a threaded engagement. The locking element 274 may then be rotated in a clockwise direction to advance the locking element 274 onto the head of the anchor 266. Rotation in a counterclockwise direction could cause the locking element 274 to retreat up into the head 266, allowing for disengagement and removal if necessary.

FIGS. 42-48 illustrate an implant 300 according to a sixth example embodiment of a hyper-lordotic implant. The implant 300 shares many similar features with the implants 200, 230, 248, 250, and 260 such that repeat discussion is not necessary. The implant 300 differs from the implants embodiments described above in that implant is configured for fixed engagement to each or the adjacent vertebral bodies (i.e. V1 and V2). Specifically, the implant 300 includes a tab 304 extending vertically above the top surface of the implant and a second tab 304 extending below the bottom surface of the implant. Each tab 304 includes a fixation aperture 305 for receiving a fixation anchor 302 therethrough to for anchoring into the vertebral bone to secure the placement of the implant. In use, when the implant 300 is positioned within the disc space, the tabs 304 engage the exterior of the upper and lower vertebra and a fixation anchor 302 is driven into the side of each of the upper or lower vertebra. A locking element in the form of a canted coil 306 is also depicted. The canted coil 306 resides in a groove formed within the fixation aperture. A ridge 308 on the head of the anchor 302 has a tapered lower surface and a generally flat upper surface such that the inner diameter of the canted coil 306 expands, due to engagement with the tapered surface of the ridge 308 as the anchor is advanced, allowing the anchor to pass. When the ridge 308 advances past the canted coil 306 the inner diameter of the coil returns to the original dimension, preventing the anchor from backing out of the fixation aperture 305.

The hyper-lordotic implants 200, 230, 248, 250, 260, and 300 have been shown, by way of example, according to a number of embodiments. It should be understood, however, that the description herein of specific embodiments is not intended to limit the scope to the particular forms disclosed, but on the contrary, the invention is to cover all modifications, equivalents, and alternatives falling within the scope and spirit of the invention as defined herein. By way of example, one will appreciate that the various quantities, sizes, shapes and locking elements/anchors of the tabs described for fixing the implants to the spine, as well as additional possible quantities, sizes, shapes and locking mechanisms/anchors not described, may be combined in any number of different configurations that can provide for a hyper-lordotic implant that can be fixed in position relative to the spine.

With reference to FIG. 49-51, an exemplary insertion instrument 310 is a described. The insertion instrument 310 includes a handle 312, a thumbwheel housing 314, an elongate tubular element 316, an inserter shaft (not shown), and a distal inserter head 318.

The handle 312 is generally disposed at the proximal end of the insertion instrument 310. The handle 312 may be further equipped with a universal connector to allow the attachment of accessories for ease of handling of the insertion instrument 310 (e.g. a straight handle or a T-handle, not shown). The handle 312 is fixed to the thumbwheel housing 314 allowing easy handling by the user. By way of example, the thumbwheel housing 314 holds at least one thumbwheel 320, and at least one spacer (not shown). Because the handle 312 is fixed, the user has easy access to the thumbwheel 320 and can stably turn the thumbwheel 320 relative to the thumbwheel housing 314. Additionally, the relative orientation of the thumbwheel 320 to the handle 312 orients the user with respect to the distal insertion head 318. The inserter shaft (not shown) is attached to the thumbwheel 320 and is freely rotatable with low friction due to the spacer. The user may then employ the thumbwheel to rotate the inserter shaft thereby advancing it towards the distal inserter head 318.

The elongate tubular element 316 is generally cylindrical and of a length sufficient to allow the device to span from the surgical target site to a location sufficiently outside the patient's body so the handle 312 and thumbwheel housing 314 can be easily accessed by a surgeon or a complimentary controlling device. The elongate tubular element 316 is dimensioned to receive a spring (not shown) and the proximal end of the inserter shaft into the inner bore 322 of the elongate tubular element 316. The elongate tubular element 316 is further configured to be snugly received within the inner recess 336 of the snap-fit channel 330 of the guided clip attachment 338 which will be explained in further detail below. The distal inserter head 318 is comprised of a threaded connector 324 and a plate 326. The threaded connector 324 is sized and dimensioned to be threadably received by the receiving aperture 104. Further, the plate 326 is sized and dimensioned to be snugly received within the grooved purchase region 106.

Figure 52:
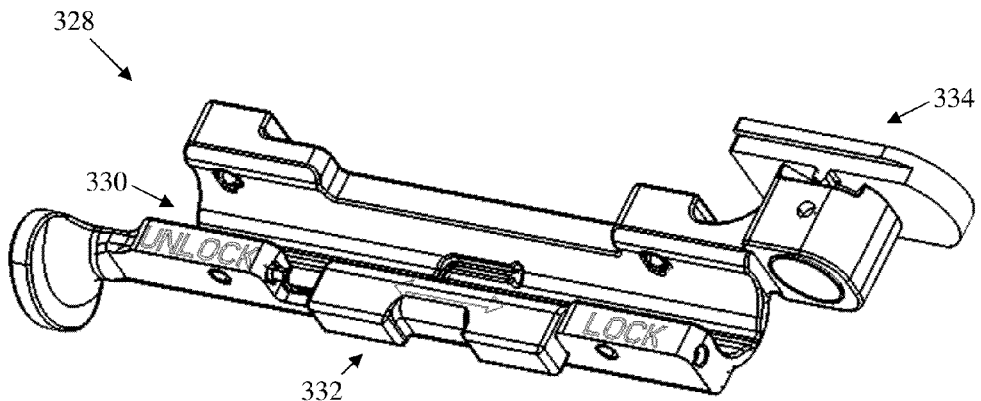
FIG. 52 is a perspective view of a guided clip attachment that can be attached to the insertion instrument of FIG. 49 for guiding the insertion of the implant along a path defined by the tissue retractor assembly of FIG. 3, according to one example embodiment.
Figure 53:
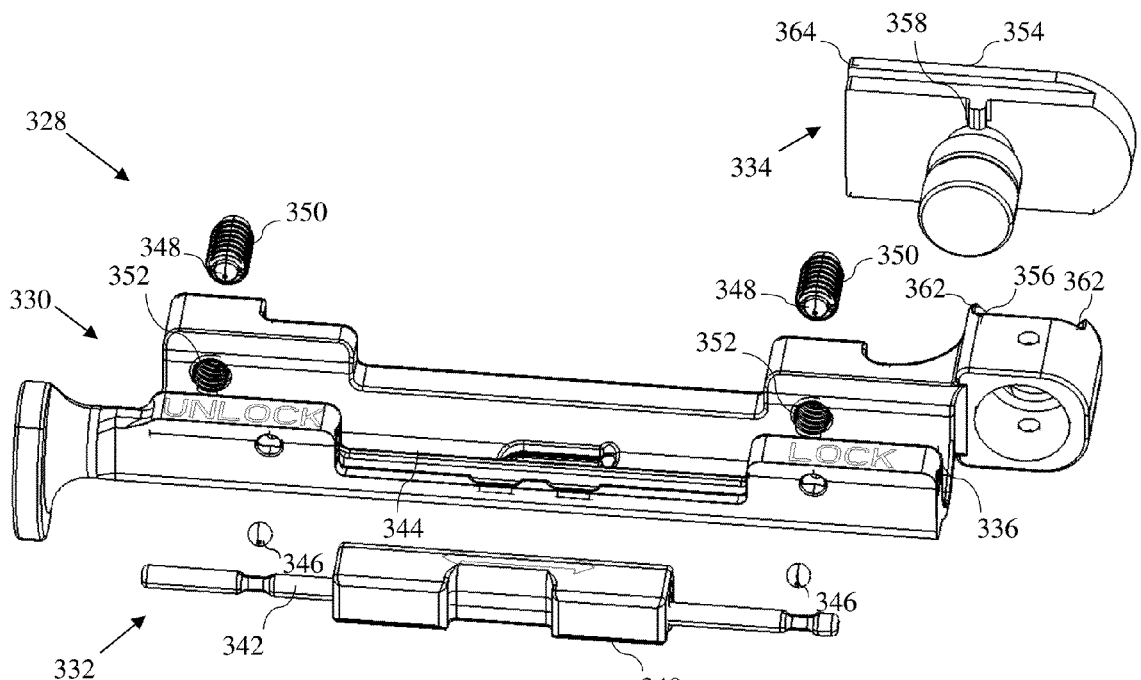
FIG. 53 is an exploded view of the guided clip attachment of FIG. 52.
Figure 54:
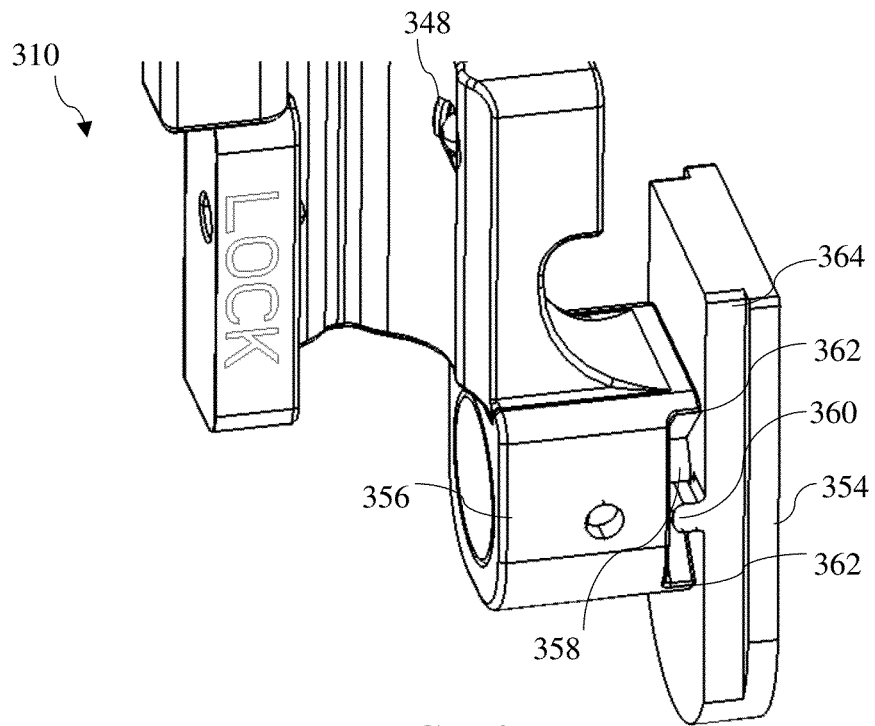
FIG. 54 is an enlarged view of an attachment base of the guided clip attachment of FIG. 52.
Figure 55:
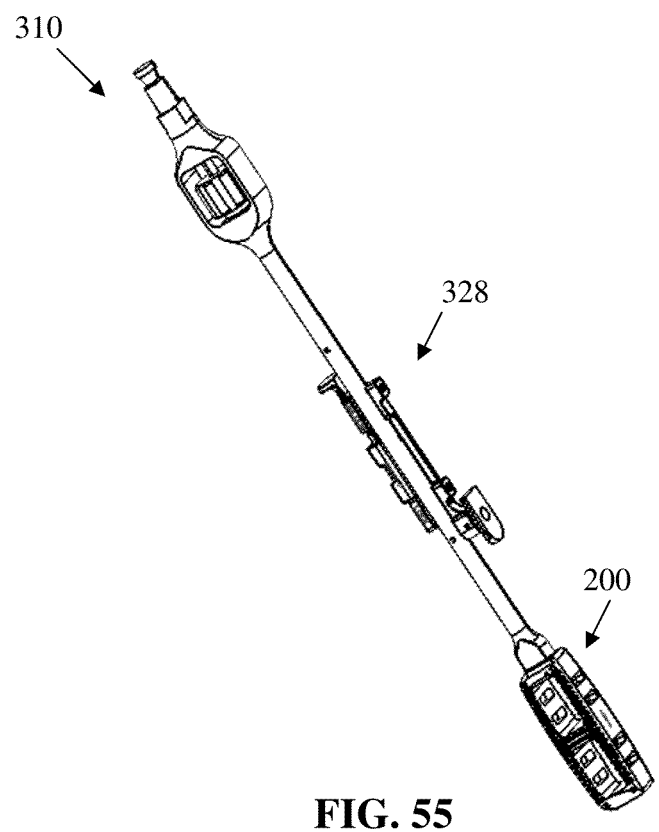
FIG. 55 is a perspective view of the guided clip attachment of FIG. 52 coupled to the insertion instrument of FIG. 49 which is coupled to the implant of FIG. 24.
Figure 56:
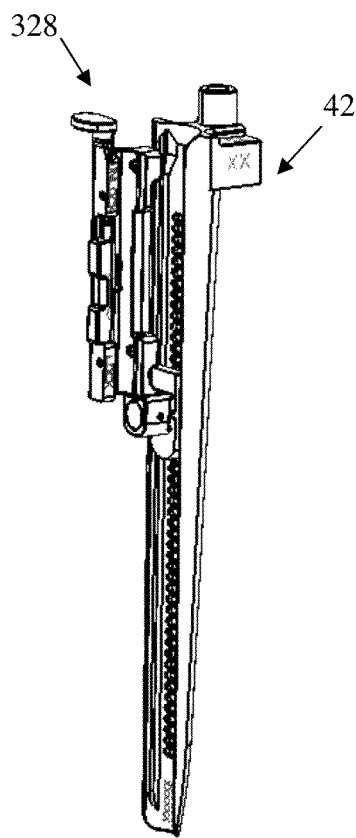
FIG. 56 is side view of the guided clip attachment of FIG. 52 engaged with a retractor blade of the tissue retractor assembly of FIG. 3.
Figure 57:
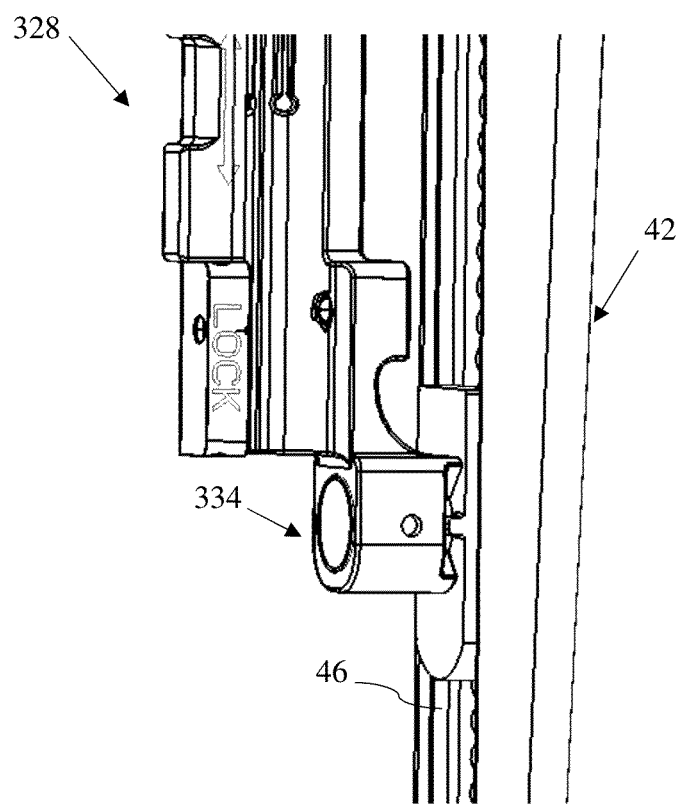
FIG. 57 is an enlarged view of the guided clip attachment of FIG. 52 engaged with a retractor blade of the tissue retractor assembly of FIG. 3.
Figure 58:
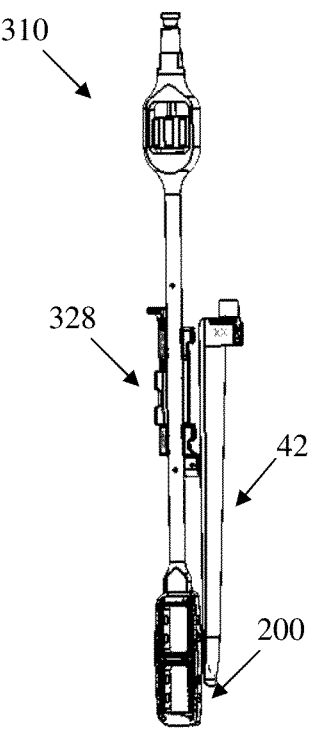
FIG. 58 is a side view of the guided clip attachment, inserter, and implant of FIG. 55 engaged with a retractor blade of the tissue retractor assembly of FIG. 3.

According to one example the insertion instrument 310 may be used in combination with a guided clip attachment 328 that engages a retractor blade 38 of the retractor assembly 36 to facilitating proper orientation and positioning of a hyper-lordotic implant, for example hyper-lordotic implant 200 as shown, or any of the various hyper-lordotic implant embodiments described herein. As illustrated in FIGS. 52-54, the guided clip attachment 328 includes a snap-fit channel 330, a locking element 332, and an attachment base 334. The snap-fit channel 330 contains an inner recess 336 that is generally arch-shaped and is sized and dimensioned to snugly receive at least a portion of the length of the elongate tubular element 316 of the insertion instrument 310. The snap-fit channel 330 may also be provided with at least one aperture 338 for receiving a ball 346 from the locking element 332 as will be described in greater detail below. The locking element 332 may be comprised of any suitable mechanism for restricting movement of the inserter instrument 310 relative to the guided clip attachment 328, including but not limited to the ball detent mechanism described. As depicted in FIG. 52, the locking mechanism may preferably include a slide lock having a sliding bar 340 with locking rod extensions 342 extending therefrom on either side. The rod extensions 342 each include a detent 343 situated along a portion of the rod extension 342. The locking rod extensions 342 are situated in and slidable within an inner groove 344 of the locking element 332. In the unlocked position the detents 345 align with the balls 346 such that the balls 346 may be depressed into the detents 345 (such that they do not extend into the channel 330) as the tubular element 316 of the insertion instrument 310 passes the balls 346 during insertion into the channel 330. In the locked position the balls 346 do not align with the detents 345 and thus cannot be depressed fully into the ball apertures. The balls 346 thus protrude into the channel 330 over the tubular body 316, preventing removal of the tubular body 316.

In addition to the locking mechanism 332, one or more ball plungers 348 may also be provided within the snap-fit channel 330 to provide greater stability and control of the guided clip attachment 328 relative to the insertion instrument 310. The ball plunger 348 may be further provided with a threaded screw 350 surrounding it, thereby creating a spring-loaded ball detent mechanism. The ball-plunger components 348, 350 are disposed within, and protrude from, at least one aperture 352 located on the inner recess 336 of the guided clip attachment 328. When the guided clip attachment 328 is attached to the elongate tubular element 316 of the inserter instrument 310, the spring-loaded ball components 348, 350 retract into the aperture 352 to allow the elongate tubular element 316 to be fully captured while still providing friction between the guided clip attachment 328 and the elongate tubular element 316 portion of the insertion instrument 310.

The guided clip attachment 328 further includes an attachment base 334 for coupling with a retractor blade (e.g. retractor blades, 38, 40, or 42) as will be explained below. This attachment provides stability for the implant 200 to be inserted and to prevent the implant 200 from migrating anteriorly during insertion. The attachment base 334 is comprised of a shim 354 and a stabilizing arm 356. The shim 354 is capable of rotating in two axes via an internal polyaxial joint 358 that allows for cephalad-caudal and anterior-posterior positioning of the implant 328. Further, the stabilizing arm 356 contains cut-out regions 362 to limit the amount of rotation in the cephalad-caudal directions. The cut-out regions 362 may be sized and figured to allow for any pre-determined amount of rotation between 1 and 359 degrees. According to one example, the cut-outs are configured to allow for rotation within the range of 10 to 30 degrees. Steps 360 engage the ends of the cutout region to prevent further rotation and also rest against the stabilizing arm 356 to prevent lateral rocking of the shim. Alternatively, cutout regions 362 may be removed and the shim may be allowed to rotate 360 degrees. The shim 354 has at least one notch 364 that is sized and dimensioned to snugly mate with the track 46 (specifically the dove tail grooves 48 formed on the interior of retractor blade 42) and may travel up and down the length of the retractor blade 38.

Figure 59:
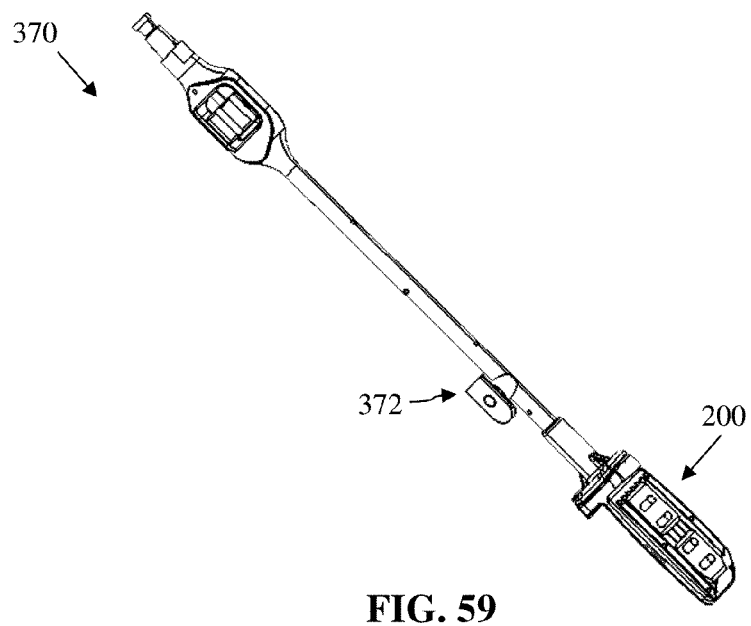
FIG. 59 is a perspective view of an inserter instrument with an integrated attachment clip, according to an embodiment of the present invention.
Figure 60:
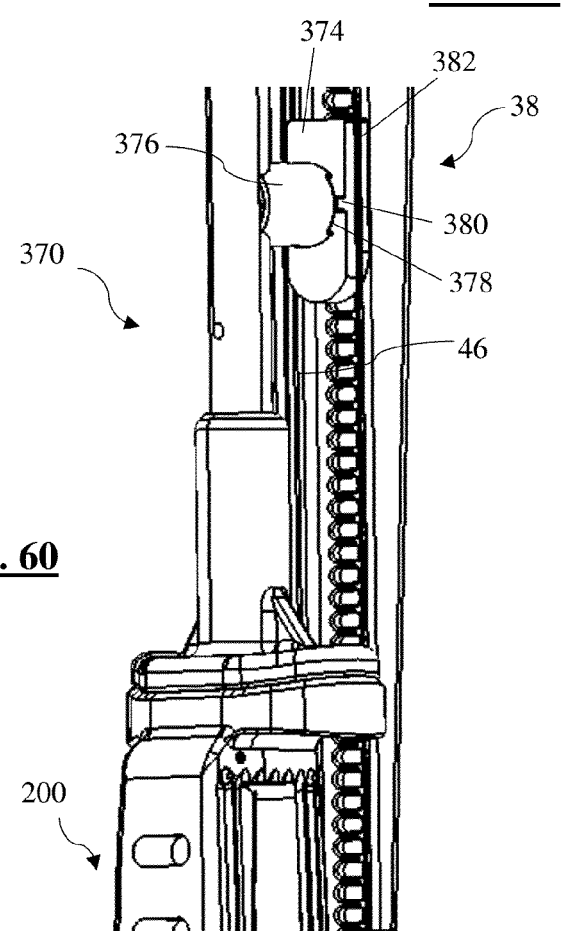
FIG. 60 is a side angle enlarged view of the inserter of FIG. 59 engaged with a retractor blade of the tissue retractor assembly of FIG. 3.
Figure 61:
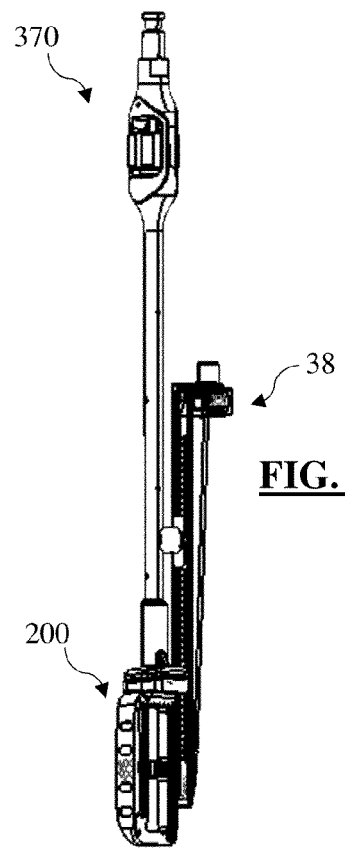
FIG. 61 is a side angle view of the inserter of FIG. 59 engaged with a retractor blade of the tissue retractor assembly of FIG. 3.

According to another example embodiment depicted in FIGS. 59-61, an inserter instrument 370 that is similar to the inserter 310 except that it is equipped with an integrated guide clip 372 is provided. Like the guided clip attachment 328, the guide clip 372, As the guided clip 372 provides additional stability and positioning assistance during insertion of the implant. The guide clip 372 includes a shim 374 and a stabilizing arm 376. The shim 354 is capable of rotating in two axes via an internal polyaxial joint (not shown) that allows for cephalad-caudal and anterior-posterior positioning of the implant. The stabilizing arm 376 may contain cut-out regions 378 to limit the amount of rotation in the cephalad-caudal directions. The cut-out regions 378 may be sized and figured to allow for any pre-determined amount of rotation between 1 and 359 degrees. According to one example, the cut-outs are configured to allow for rotation within the range of 10 to 30 degrees. Steps 380 engage the ends of the cutout region to prevent further rotation and also rest against the stabilizing arm 376 to prevent lateral rocking of the shim. Alternatively, cutout regions 378 may be removed and the shim may be allowed to rotate 360 degrees. The shim 374 has at least one notch 382 that is sized and dimensioned to snugly mate with the track 46 (specifically the dove tail grooves 48 formed on the interior of retractor blade 38) and may travel up and down the length of the retractor blade 38.

Figure 62:
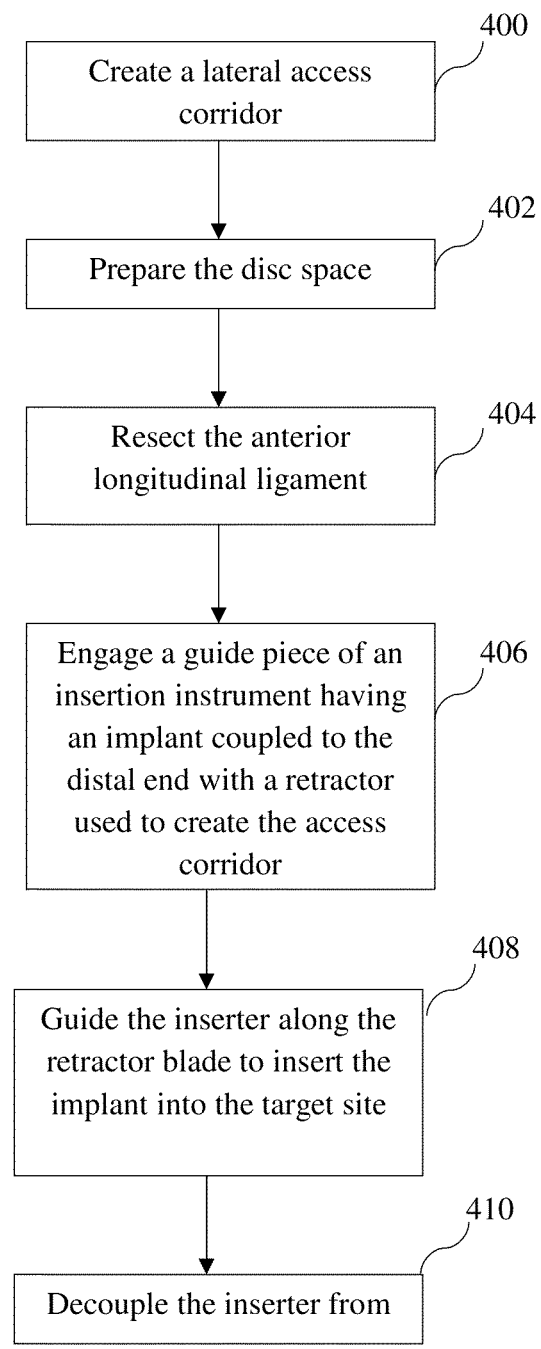
FIG. 62 is a flow chart indicating the steps utilized to restore lordosis to the spine of a patient, according to one example method.

As depicted in the flowchart of FIG. 62, one example method for utilizing the systems, implants, and instruments described above is set forth below. A lateral access surgical corridor is formed in the patient (step 400), the disc space is prepared (step 402), and the anterior longitudinal ligament is resected (step 404) as previously explained. Next, at step 406, a guided clip associated with the insertion instrument (either integral to or removably coupled to) is engaged with the track on a retractor blade used to create the access corridor. The implant is then inserted into the disc space (step 408) as the guide clip translates down the track in the retractor blade. Adjustments can be made to the implant insitu as needed while minimizing the likelihood that the implant 200 will be expelled from its optimal position. At step 410 the inserter can be decoupled from the implant 200 and removed from the access corridor. Depending on the type of hyper-lordotic implant selection, an additional step of securing the implant with fixation anchors may also be appropriate. Having been deposited in the disc space, the implant facilitates spinal fusion over time by maintaining the restored curvature as natural bone growth occurs through and/or past the implant, resulting in the formation of a boney bridge extending between the adjacent vertebral bodies.

While this invention has been described in terms of a best mode for achieving this invention's objectives, it will be appreciated by those skilled in the art that variations may be accomplished in view of these teachings without deviating from the spirit or scope of the invention. For example, particularly at L5-S1 where the pelvic bone makes a lateral access approach difficult, an antero-lateral approach similar to the approach utilized during appendectomies may be utilized.

What is claimed is:

1. A method for correcting sagittal imbalance of a lumbar spine, comprising the steps of:
   a) creating an operative corridor that provides access to a targeted spinal disc via a lateral approach by inserting an access system along a lateral, trans-psoas path to the targeted spinal disc, the access system comprising a stimulation electrode that is inserted under conditions wherein an electrical stimulation signal is delivered through said stimulation electrode for nerve monitoring when the stimulation electrode is positioned in the lateral, trans-psoas path;
   b) inserting a cutting device through the lateral operative corridor and severing the Anterior Longitudinal Ligament (ALL); and
   c) connecting an insertion instrument to a first retractor blade forming a portion of the border of the operative corridor, the insertion instrument having an implant for positioning between the adjacent vertebral bodies bordering the targeted disc space coupled thereto; and d) advancing the insertion instrument along the retractor blade to position the implant between the adjacent vertebral bodies.

2. The method of claim 1, wherein the cutting device includes a blade.

3. The method of claim 2, wherein the blade is situated between two finger extensions.

4. The method of claim 1, wherein the cutting device includes an anode electrode.

5. The method of claim 4, wherein an insulated retractor is positioned between the ALL and the great vessels prior to activating electrical current that cuts the ALL.

6. The method of claim 1, wherein the implant has an upper surface to contact a first vertebra of the adjacent vertebrae when the implant is positioned within the interbody space, a lower surface to contact a second vertebra of the adjacent vertebrae when the implant is positioned within the interbody space, a distal wall, a proximal wall, an anterior sidewall that faces anteriorly when the implant is positioned within the interbody space, and a posterior sidewall that faces posteriorly when the implant is positioned within the interbody space, the implant further having a maximum longitudinal length extending from a proximal end of the proximal wall to a distal end of the distal wall, a width extending from the anterior end of the anterior sidewall to the posterior end of the posterior sidewall, the maximum longitudinal length being at least 40 mm, an anterior height extending from the upper surface to the lower surface at the anterior sidewall and a posterior height extending from the upper surface to the lower surface at the posterior sidewall, the anterior height being greater than the posterior height such that the upper and lower surfaces increase in slope from the posterior sidewall to the anterior sidewall forming an angle at least 20 degrees.

7. The method of claim 6, including the additional step of anchoring the implant in position between the first vertebra and second vertebra.

8. The method of claim 7, wherein the proximal sidewall includes an extension tab that abuts a lateral aspect of at least one of the first vertebra and second vertebra when the implant is positioned in the intervertebral space, the extension tab including at least one aperture and the step of anchoring the implant comprises advancing an anchor through the at least one aperture into one of the first and second vertebra.

9. The method of claim 8, wherein the extension tab includes an upper portion including a first aperture that abuts a lateral aspect of the first vertebra and a lower portion including a second aperture that abuts a lateral aspect of the second vertebra, and wherein the step of anchoring the implant comprises advancing an anchor through the first aperture into the first vertebra and advancing a second anchor through the second aperture into the second vertebra.

10. The method of claim 6, wherein the upper surface and lower surface are planar surfaces.

11. The method of claim 6, wherein the upper surface and lower surfaces are convex surfaces.

12. The method of claim 6, wherein the implant is a fusion implant and includes at least one fusion aperture opening in the upper surface and lower surface to permit bone growth between the first vertebra and second vertebra.

13. The method of claim 12, comprising the additional step of depositing bone growth promoting substances within the at least one fusion aperture before, during, and/or, after advancing the implant into the intervertebral disc space.

14. The method of claim 6, wherein the top surface includes anti-migration features that contact the first vertebra and the bottom surface includes anti-migration features that contact the lower vertebra.

15. The method of claim 1, wherein the step of severing the ALL comprises protecting the great vessels while the ALL is being severed.

16. The method of claim 1, wherein the access system comprises at least one dilator having the stimulation electrode situated on a distal end and a retractor that slides over the at least one dilator in a first configuration, and thereafter adjusts to a second configuration to form the operative corridor, wherein the retractor includes the first retractor blade.

17. The method claim 16, wherein the nerve monitoring includes determining a proximity and direction to a nerve located in the psoas muscle.

18. The method of claim 17, wherein the nerve monitoring is used to position the initial dilator as posterior as possible while remaining anterior to the nerve.

19. The method of claim 18, wherein the retractor includes a plurality of blades, one of the plurality of blades being a posterior blade and comprising the additional step of fixing the position of the posterior blade just anterior to the nerve prior to adjusting to the second configuration such that adjusting to the second configuration comprises moving at least one of the plurality of blades away from the posterior blade.

20. The method of claim 19, wherein the first retractor blade is the posterior retractor blade.

21. The method of claim 20, wherein connecting the insertion instrument to the first retractor blade includes slideably engaging a guide piece of the insertion instrument into a track of the first retractor blade.

22. The method of claim 21, wherein the guide piece rotates in two axes relative to a longitudinal axis of the insertion instrument such that the anterior-posterior position and cephalad-caudal position of the implant is adjustable relative to the first retractor blade.

* * * * *